United States Patent
Hefner et al.

(10) Patent No.: US 11,248,260 B2
(45) Date of Patent: Feb. 15, 2022

(54) QUANTITATIVE AMPLIFICATION NORMALIZATION WITH QUENCHERS

(71) Applicant: Bio-Rad Laboratories, Inc., Hercules, CA (US)

(72) Inventors: Eli Hefner, Fairfield, CA (US); Yann Jouvenot, Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 276 days.

(21) Appl. No.: 16/353,865

(22) Filed: Mar. 14, 2019

(65) Prior Publication Data

US 2019/0284610 A1 Sep. 19, 2019

Related U.S. Application Data

(60) Provisional application No. 62/643,506, filed on Mar. 15, 2018.

(51) Int. Cl.
  *C12Q 1/686* (2018.01)
  *C12Q 1/6818* (2018.01)
  *C12Q 1/70* (2006.01)
  *C12Q 1/6806* (2018.01)

(52) U.S. Cl.
  CPC ........... *C12Q 1/686* (2013.01); *C12Q 1/6806* (2013.01); *C12Q 1/701* (2013.01); *C12Q 1/6818* (2013.01)

(58) Field of Classification Search
  CPC . C12Q 1/6851; C12Q 2563/107; C12Q 1/686
  See application file for complete search history.

(56) References Cited

U.S. PATENT DOCUMENTS

| | | | |
|---|---|---|---|
| 6,323,337 | B1 | 11/2001 | Singer et al. |
| 2006/0292571 | A1 | 12/2006 | Babiel et al. |
| 2015/0184232 | A1 | 7/2015 | Li et al. |
| 2018/0251829 | A1* | 9/2018 | Hassibi .............. G01N 21/6428 |

OTHER PUBLICATIONS

International Search Report and Written Opinion from PCT/US2019/022332 dated Aug. 19, 2019; 13 pages.
Extended European Search Report in EP Appln. 19768209.9 dated Nov. 19, 2021; 9 pages.
Miotto, E. et al.; "Quantification of Circulating miRNAs by Droplet Digital PCR: Comparison of EvaGreen- and TaqMan-Based Chemistries"; *Cancel Epidemiology, Biomarkers & Prevention*; vol. 23, No. 12; Dec. 1, 2014; pp. 2638-2642.

* cited by examiner

*Primary Examiner* — Teresa E Strzelecka
(74) *Attorney, Agent, or Firm* — Kilpatrick Townsend and Stockton LLP

(57) ABSTRACT

Compositions, kits, and methods are provided for the normalization of a quantitative polymerase chain reaction (PCR) amplification. Also provided are compositions, kits, and methods for multiplexing qPCR amplification of two or more target nucleic acids in the same well.

20 Claims, 10 Drawing Sheets

Specification includes a Sequence Listing.

SYBR green Cq = Fluorescence from gene of interest

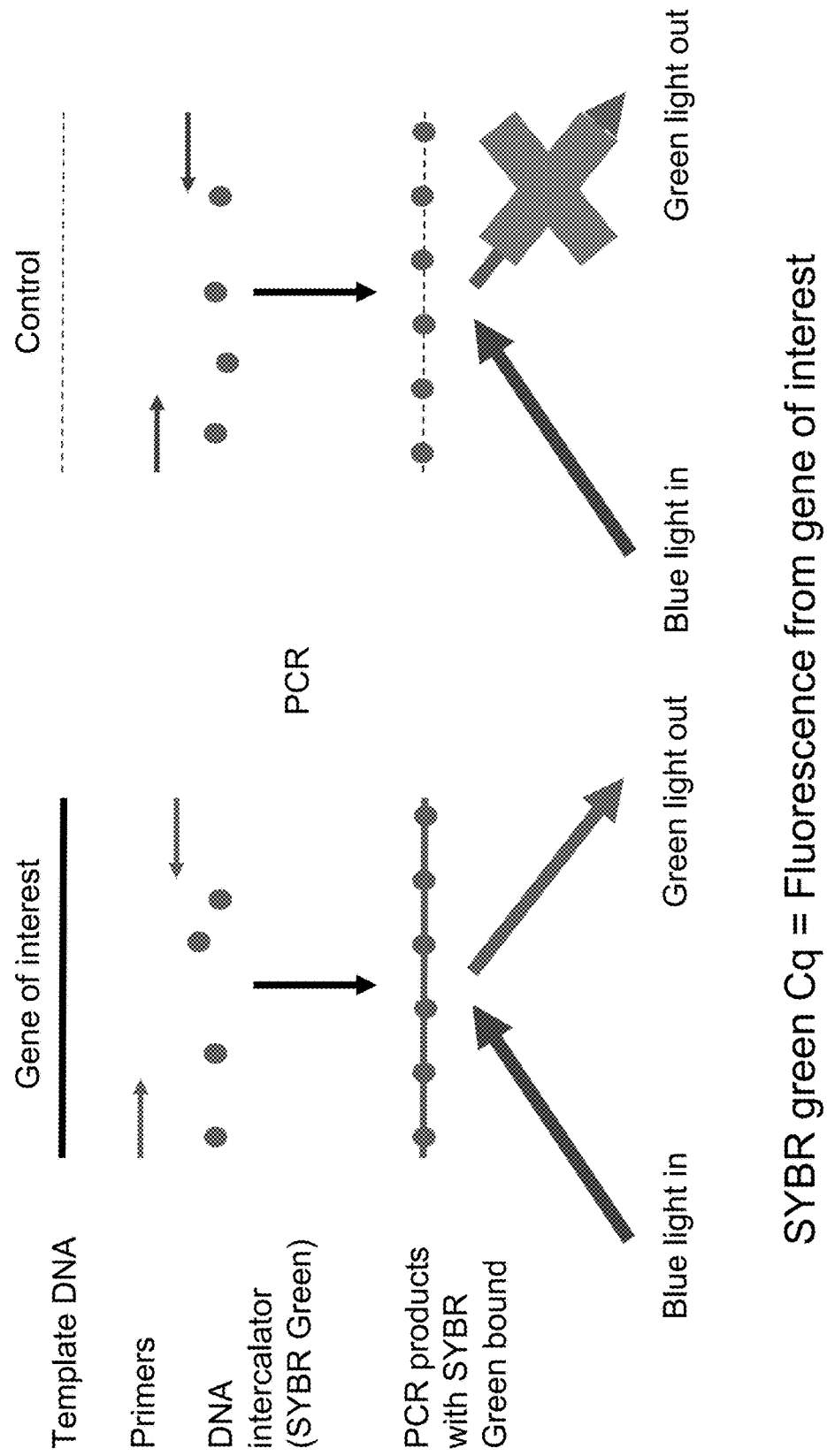

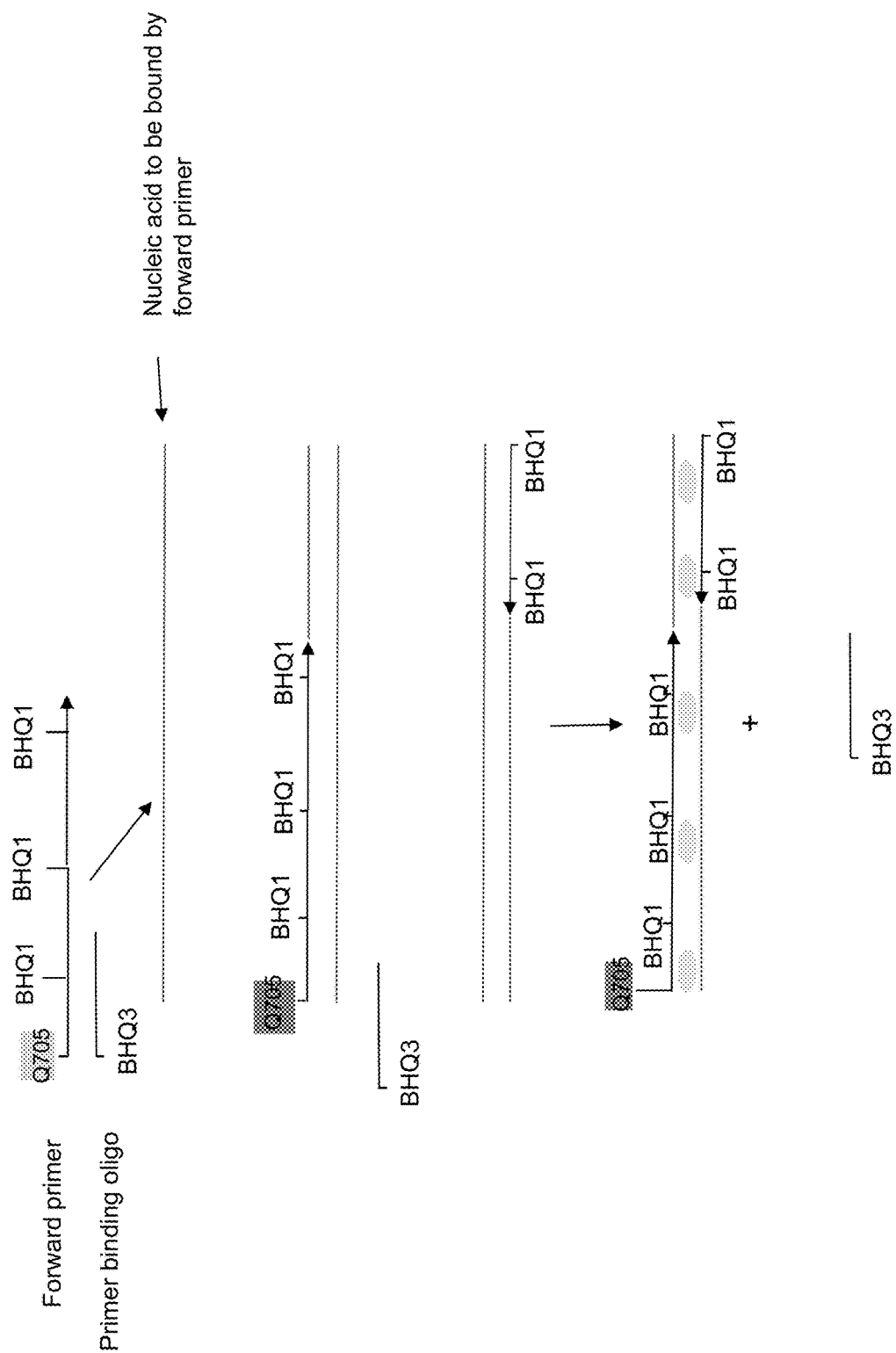

QUANTITATIVE AMPLIFICATION NORMALIZATION WITH QUENCHERS

CROSS-REFERENCE TO RELATED APPLICATIONS

This application claims priority to U.S. Provisional Application No. 62/643,506, filed Mar. 15, 2018, the entire content of which is incorporated by reference herein.

SEQUENCE LISTING SUBMITTED AS ASCII TEXT FILE

The instant application contains a Sequence Listing that has been submitted electronically in ASCII format and is hereby incorporated by reference in its entirety. Said ASCII copy, created on Aug. 18, 2021 is named 094263-1128460-116310US_SL.txt and is 699 bytes in size.

BACKGROUND OF THE INVENTION

Quantitative polymerase chain reaction (qPCR) under optimized conditions generates quantitative results based on fluorogenesis during the PCR reaction. The primary methods of fluorogenesis are enzymatic cleavage of a probe or dye intercalation into double-stranded DNA. The accuracy of quantitation can be affected by various factors, including reaction efficiency or the presence of an inhibitor. Skewed reaction efficiency in an experimental sample, relative to a control, can lead to over- or under-quantitation.

BRIEF SUMMARY OF THE INVENTION

In one aspect, compositions, kits, and methods for normalizing a qPCR amplification are provided. In some embodiments, a composition for normalizing a qPCR amplification comprises:
 a set of fluorescence quenching primers that specifically bind to a control nucleic acid, the set comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the control nucleic acid; and
 a detectable probe that specifically associates with the control nucleic acid.

In some embodiments, the forward quenching primer and/or the reverse quenching primer comprises two quenchers. In some embodiments, the forward quenching primer and/or the reverse quenching primer comprises more than two quenchers (e.g., 3, 4, 5, or more quenchers). In some embodiments, the distance between the quenchers does not exceed the Förster radius of the fluorophore that is quenched by the quenchers.

In some embodiments, the composition comprises:
 a set of fluorescence quenching primers that specifically bind to a control nucleic acid, the set comprising a forward quenching primer and a reverse quenching primer, wherein each of the forward quenching primer and the reverse quenching primer comprises a first quencher at or near the 5' end of the primer and a second quencher near the 3' end of the primer; and
 a detectable probe that specifically associates with the control nucleic acid.

In some embodiments, the composition comprises:
 a set of fluorescence quenching primers that specifically bind to a control nucleic acid, the set comprising a forward quenching primer and a reverse quenching primer, wherein each of the forward quenching primer and the reverse quenching primer comprises a first quencher at or near the 5' end of the primer and a second quencher near the 3' end of the primer;
 a detectable probe that specifically associates with the control nucleic acid; and
 the control nucleic acid, wherein the control nucleic acid comprises a forward primer binding site to which the forward quenching primer binds, a probe binding site to which the probe binds, and a reverse primer binding site to which the reverse quenching primer binds.

In some embodiments, for the forward quenching primer, the first quencher is at the 5' end or is within 5 bases from the 5' end and the second quencher is within 5-10 bases from the 3' end. In some embodiments, for the forward quenching primer, the first quencher and the second quencher are separated by up to about 25 bases. In some embodiments, for the reverse quenching primer, the first quencher is at the 5' end or is within 5 bases from the 5' end and the second quencher is within 5-10 bases from the 3' end. In some embodiments, for the reverse quenching primer, the first quencher and the second quencher are separated by up to about 25 bases. In some embodiments, the first quencher and the second quencher are a a dark quencher a non-fluorescent chromophore Black Hole Quencher®-1 (BHQ-1) quencher.

In some embodiments, the composition further comprises a fluorescent DNA intercalator. In some embodiments, the fluorescent DNA intercalator is SYBR® Green I, EvaGreen®, PicoGreen®, ethidium bromide, SYBR® Gold, YOYO®, YO-PRO™, TOTO®, 4-[6-(Benzoxazol-2-yl)-dihydro-3-methyl-2(3H)-benzothiazolylidenemethyl]-1-methylquinolinium iodide (BOXTO™), or 4-[(3-methyl-6-(benzothiazol-2-yl)-2,3-dihydro-(benzo-1,3-thiazole)-2-methylidene)]-1-methyl-pyridinium iodide (BEBO™). In some embodiments, the fluorescent DNA intercalator is SYBR® Green I.

In some embodiments, the detectable probe specifically binds (e.g., directly binds) to the control nucleic acid.

In some embodiments, the detectable probe is attached to an oligonucleotide. In some embodiments, the detectable probe is attached to one or both of the fluorescence quenching primers that specifically bind to the control nucleic acid. In some embodiments, the detectable probe is attached to the forward quenching primer. In some embodiments, the detectable probe is attached to the reverse quenching primer. In some embodiments, wherein the detectable probe is attached to the forward quenching primer or the reverse quenching primer, the composition further comprises an oligonucleotide that hybridizes to a portion of the primer, wherein the oligonucleotide comprises a quencher that quenches the signal emitted by the detectable probe. In some embodiments, the detectable probe is attached to an oligonucleotide that hybridizes to a portion of either the forward quenching primer or the reverse quenching primer. In some embodiments, the detectable probe is attached to an oligonucleotide that hybridizes to a portion of either the forward quenching primer or the reverse quenching primer, and the primer to which the oligonucleotide hybridizes further comprises a quencher that quenches the signal emitted by the detectable probe. In some embodiments, the detectable probe is attached to an oligonucleotide that hybridizes to a portion of either the forward quenching primer or the reverse quenching primer, and the oligonucleotide further comprises a quencher that quenches the signal emitted by the detectable probe.

In some embodiments, the detectable probe comprises a fluorescent dye having an emission spectrum that is distinguishable from the emission spectrum of the fluorescent DNA intercalator. In some embodiments, the detectable probe comprises a fluorescent dye selected from the group consisting of Cy3™, Cy5™, FAM™, HEX™ JOE™, QUASAR®, rhodamine, ROX™, TAMRA™, TET™, Texas Red™, TYE™, and VIC™. In some embodiments, the detectable probe comprises a QUASAR® fluorescent dye. In some embodiments, the detectable probe comprises a hydrolysis probe.

In some embodiments, the composition further comprises one or more buffers, salts, nucleotides, primers, polymerases, and/or water.

In some embodiments, the composition is a solution. In some embodiments, the composition is lyophilized.

In another aspect, solid supports for use in normalizing a qPCR amplification are provided. In some embodiments, the solid support comprises one or more partitions, wherein each of the one or more partitions comprises a composition (e.g., a lyophilized composition) as disclosed herein.

In another aspect, kits for use in normalizing a qPCR amplification are provided. In some embodiments, the kit comprises a composition or solid support as disclosed herein.

In another aspect, methods for normalizing a qPCR amplification to a control are provided. In some embodiments, the method comprises:
  combining a target nucleic acid and a control nucleic acid with (i) a fluorescent DNA intercalator, (ii) a set of target nucleic acid-specific primers comprising a target nucleic acid-specific forward primer and a target nucleic acid-specific reverse primer, (iii) a detectable probe that specifically associates with the control nucleic acid, and (iv) a set of fluorescence quenching primers that specifically bind to a control nucleic acid comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the control nucleic acid (control nucleic acid amplicon), thereby forming a reaction mixture;
  incubating the reaction mixture under conditions suitable to generate a target nucleic acid amplicon and a control nucleic acid amplicon, wherein the fluorescent DNA intercalator binds to both the target nucleic acid amplicon and the control nucleic acid amplicon and wherein the control nucleic acid amplicon that is generated comprises a plurality of quenchers incorporated into the amplicon;
  exciting the fluorescent DNA intercalator (e.g., using an excitation light source), wherein the quenchers that are incorporated into the control nucleic acid amplicon quench at least a portion of the fluorescence emitted by the fluorescent DNA intercalator bound to the control nucleic acid amplicon; and
  detecting the target nucleic acid amplicon and the control nucleic acid amplicon, wherein the target nucleic acid amplicon is detected by detecting the fluorescent signal emitted by the fluorescent DNA intercalator and wherein the control nucleic acid amplicon is detected by detecting the detectable probe.

In some embodiments, the method comprises:
  combining a target nucleic acid and a control nucleic acid with (i) a fluorescent DNA intercalator, (ii) a set of target nucleic acid-specific primers comprising a target nucleic acid-specific forward primer and a target nucleic acid-specific reverse primer, (iii) a detectable probe that specifically associates with the control nucleic acid, and (iv) a set of fluorescence quenching primers that specifically bind to a control nucleic acid comprising a forward quenching primer and a reverse quenching primer, wherein each of the forward quenching primer and the reverse quenching primer comprises a first quencher at or near the 5' end of the primer and a second quencher near the 3' end of the primer, thereby forming a reaction mixture;
  incubating the reaction mixture under conditions suitable to generate a target nucleic acid amplicon and a control nucleic acid amplicon, wherein the fluorescent DNA intercalator binds to both the target nucleic acid amplicon and the control nucleic acid amplicon and wherein the control nucleic acid amplicon that is generated comprises a plurality of quenchers incorporated into the amplicon;
  exciting the fluorescent DNA intercalator (e.g., using an excitation light source), wherein the quenchers that are incorporated into the control nucleic acid amplicon quench at least a portion of the fluorescence emitted by the fluorescent DNA intercalator bound to the control nucleic acid amplicon; and
  detecting the target nucleic acid amplicon and the control nucleic acid amplicon, wherein the target nucleic acid amplicon is detected by detecting the fluorescent signal emitted by the fluorescent DNA intercalator and wherein the control nucleic acid amplicon is detected by detecting the detectable probe.

In some embodiments, for the forward quenching primer and/or for the reverse quenching primer, the first quencher is at the 5' end or is within 5 bases from the 5' end and the second quencher is within 5-10 bases from the 3' end. In some embodiments, for the forward quenching primer and/or for the reverse quenching primer, the first quencher and the second quencher are separated by up to about 25 bases.

In some embodiments, the detectable probe comprises a fluorescent dye having an emission spectrum that is distinguishable from the emission spectrum of the fluorescent DNA intercalator. In some embodiments, wherein the detectable probe emits a fluorescent signal that is distinguishable from the signal emitted by the fluorescent DNA intercalator, the method further comprises exciting the detectable probe and detecting the fluorescent signal emitted by the detectable probe. In some embodiments, the fluorescent DNA intercalator is SYBR® Green I, EvaGreen®, PicoGreen®, ethidium bromide, SYBR® Gold, YOYO®, YO-PRO™, TOTO®, BOXTO, or BEBO. In some embodiments, the detectable probe comprises a fluorescent dye selected from the group consisting of Cy3™ Cy5™, FAM™, HEX™ JOE™, QUASAR®, rhodamine, ROX™, TAMRA™, TET™Texas Red™, TYE™, and VIC™.

In some embodiments, the detectable probe directly binds to the control nucleic acid. In some embodiments, the detectable probe is attached to an oligonucleotide. In some embodiments, the detectable probe is attached to one or both of the fluorescence quenching primers that specifically bind to the control nucleic acid. In some embodiments, the detectable probe is attached to the forward quenching primer. In some embodiments, the detectable probe is attached to the reverse quenching primer. In some embodiments, wherein the detectable probe is attached to the forward quenching primer or the reverse quenching primer, the combining step further comprises combining the sample with an oligonucleotide that hybridizes to a portion of the primer and comprises a quencher that quenches the signal emitted by the detectable probe. In some embodiments, the detectable probe is attached to an oligonucleotide that hybridizes to a portion of either the forward quenching primer or the reverse quenching primer. In some embodiments, the detectable probe is attached to an oligonucleotide that hybridizes to a portion of either the forward quenching primer or the reverse quenching primer, and the primer to which the oligonucleotide hybridizes further comprises a quencher that quenches the signal emitted by the detectable probe. In some embodiments, the detectable probe is attached to an oligonucleotide that hybridizes to a portion of either the forward quenching primer or the reverse quenching primer, and the oligonucleotide further comprises a quencher that quenches the signal emitted by the detectable probe.

In some embodiments, the detecting step comprises determining the quantitation cycle (Cq) for the target nucleic acid amplicon and the control nucleic acid amplicon. In some embodiments, the detecting step comprises quantitating the amount of fluorescent signal emitted by the fluorescent DNA intercalator and the amount of signal from the detectable probe.

In still another aspect, compositions, kits, and methods for multiplexing qPCR amplification of two or more target nucleic acids in the same well are provided. In some embodiments, a composition for multiplexing qPCR amplification of two target nucleic acids comprises:
  a first target nucleic acid-specific primer set comprising a first target nucleic acid-specific forward primer and a first target nucleic acid-specific reverse primer;
  a second target nucleic acid-specific primer set comprising a forward quenching primer and a reverse quenching primer that specifically bind to the second target nucleic acid, wherein each of the forward quenching primer and the reverse quenching primer comprises two or more quenchers and wherein the two or more quenchers are positioned within the primer such that the quenchers quench all or substantially all of the fluorescence from an amplification product of the second target nucleic acid; and
  a detectable probe that specifically associates with the second target nucleic acid.

In some embodiments, the composition comprises:
  a first target nucleic acid-specific primer set comprising a first target nucleic acid-specific forward primer and a first target nucleic acid-specific reverse primer;
  a second target nucleic acid-specific primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer; and
  a detectable probe that specifically associates with the second target nucleic acid.

In some embodiments, the composition further comprises a fluorescent DNA intercalator. In some embodiments, the fluorescent DNA intercalator is SYBR® Green I, EvaGreen®, PicoGreen®, ethidium bromide, SYBR® Gold, YOYO®, YO-PRO™, TOTO®, BOXTO™ or BEBO™. In some embodiments, the fluorescent DNA intercalator is SYBR® Green I.

In some embodiments, the detectable probe directly binds to the second target nucleic acid.

In some embodiments, the detectable probe is attached to an oligonucleotide. In some embodiments, the detectable probe is attached one or both of the fluorescence quenching primers that specifically bind to the second target nucleic acid. In some embodiments, the detectable probe is attached to the forward quenching primer. In some embodiments, the detectable probe is attached to the reverse quenching primer. In some embodiments, wherein the detectable probe is attached to the forward quenching primer or the reverse quenching primer, the composition further comprises an oligonucleotide that hybridizes to a portion of the primer, wherein the oligonucleotide comprises a quencher that quenches the signal emitted by the detectable probe. In some embodiments, the detectable probe is attached to an oligonucleotide that hybridizes to a portion of either the forward quenching primer or the reverse quenching primer. In some embodiments, the detectable probe is attached to an oligonucleotide that hybridizes to a portion of either the forward quenching primer or the reverse quenching primer, and the primer to which the oligonucleotide hybridizes further comprises a quencher that quenches the signal emitted by the detectable probe. In some embodiments, the detectable probe is attached to an oligonucleotide that hybridizes to a portion of either the forward quenching primer or the reverse quenching primer, and the oligonucleotide further comprises a quencher that quenches the signal emitted by the detectable probe.

In some embodiments, the detectable probe comprises a fluorescent dye having an emission spectrum that is distinguishable from the emission spectrum of the fluorescent DNA intercalator. In some embodiments, the detectable probe comprises a fluorescent dye selected from the group consisting of Cy3™Cy5™, FAM™, HEX™ JOE™, QUASAR®, rhodamine, ROX™ TAMRA™, TET™Texas Red™ TYE™ and VIC™. In some embodiments, the detectable probe comprises a QUASAR® fluorescent dye. In some embodiments, the detectable probe comprises a hydrolysis probe.

In some embodiments, a kit for multiplexing qPCR amplification comprises a composition as disclosed herein.

In some embodiments, the method for multiplexing qPCR amplification comprises:
  combining a sample comprising a first target nucleic acid and a second target nucleic acid with (i) a fluorescent DNA intercalator, (ii) a first target nucleic acid-specific primer set comprising a first target nucleic acid-specific forward primer and a first target nucleic acid-specific reverse primer, (iii) a detectable probe that specifically associates with the second target nucleic acid, and (iv) a second target nucleic acid-specific primer set comprising a forward quenching primer and a reverse quenching primer that specifically bind to the second target nucleic acid, wherein each of the forward quenching primer and the reverse quenching primer comprises two or more quenchers and wherein the two or more quenchers are positioned within the primer such that the quenchers quench all or substantially all of the fluorescence from an amplification product of the second target nucleic acid, thereby forming a reaction mixture;
  incubating the reaction mixture under conditions suitable to generate a first target nucleic acid amplicon and a second target nucleic acid amplicon, wherein the fluorescent DNA intercalator binds to both the first target nucleic acid amplicon and the second target nucleic acid amplicon and wherein the second target nucleic acid amplicon that is generated comprises a plurality of quenchers incorporated into the amplicon;

exciting the fluorescent DNA intercalator, wherein the quenchers in the second target nucleic acid amplicon quench at least a portion of the fluorescence emitted by the fluorescent DNA intercalator bound to the second target nucleic acid amplicon; and detecting the first target nucleic acid amplicon and the second target nucleic acid amplicon, wherein the first target nucleic acid amplicon is detected by detecting the fluorescent signal emitted by the fluorescent DNA intercalator and wherein the second target nucleic acid amplicon is detected by detecting the detectable probe.

In some embodiments, the method for multiplexing qPCR amplification comprises:

combining a sample comprising a first target nucleic acid and a second target nucleic acid with (i) a fluorescent DNA intercalator, (ii) a first target nucleic acid-specific primer set comprising a first target nucleic acid-specific forward primer and a first target nucleic acid-specific reverse primer, (iii) a detectable probe that specifically associates with the second target nucleic acid, and (iv) a second target nucleic acid-specific primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer, thereby forming a reaction mixture;

incubating the reaction mixture under conditions suitable to generate a first target nucleic acid amplicon and a second target nucleic acid amplicon, wherein the fluorescent DNA intercalator binds to both the first target nucleic acid amplicon and the second target nucleic acid amplicon and wherein the second target nucleic acid amplicon that is generated comprises a plurality of quenchers incorporated into the amplicon;

exciting the fluorescent DNA intercalator, wherein the quenchers in the second target nucleic acid amplicon quench at least a portion of the fluorescence emitted by the fluorescent DNA intercalator bound to the second target nucleic acid amplicon; and detecting the first target nucleic acid amplicon and the second target nucleic acid amplicon, wherein the first target nucleic acid amplicon is detected by detecting the fluorescent signal emitted by the fluorescent DNA intercalator and wherein the second target nucleic acid amplicon is detected by detecting the detectable probe.

In some embodiments, each of the forward quenching primer and the reverse quenching primer comprises a first quencher at or near the 5' end of the primer and a second quencher near the 3' end of the primer. In some embodiments, for the forward quenching primer and/or the reverse quenching primer, the first quencher is at the 5' end or is within 5 bases from the 5' end and the second quencher is within 5-10 bases from the 3' end. In some embodiments, for the forward quenching primer and/or the reverse quenching primer, the first quencher and the second quencher are separated by up to about 25 bases.

In some embodiments, wherein the detectable probe emits a fluorescent signal that is distinguishable from the signal emitted by the fluorescent DNA intercalator, the method further comprises exciting the detectable probe and detecting the fluorescent signal emitted by the detectable probe. In some embodiments, the detectable probe comprises a hydrolysis probe. In some embodiments, the detectable probe comprises a fluorescent dye selected from the group consisting of Cy3™, Cy5™ FAM™, HEX™ JOE™, QUASAR®, rhodamine, ROX™ TAMRA™, TET™, Texas Red™ TYE™, and VIC™. In some embodiments, the fluorescent DNA intercalator is SYBR®Green I, EvaGreen® PicoGreen®, ethidium bromide, SYBR® Gold, YOYO®, YO-PRO™, TOTO®, BOXTO™, or BEBO™.

In some embodiments, the detectable probe directly binds to the second target nucleic acid. In some embodiments, the detectable probe is attached to an oligonucleotide. In some embodiments, the detectable probe is attached to one or both of the fluorescence quenching primers that specifically bind to the second target nucleic acid. In some embodiments, the detectable probe is attached to the forward quenching primer. In some embodiments, the detectable probe is attached to the reverse quenching primer. In some embodiments, wherein the detectable probe is attached to the forward quenching primer or the reverse quenching primer, the combining step further comprises combining the sample with an oligonucleotide that hybridizes to a portion of the primer and comprises a quencher that quenches the signal emitted by the detectable probe. In some embodiments, the detectable probe is attached to an oligonucleotide that hybridizes to a portion of either the forward quenching primer or the reverse quenching primer. In some embodiments, the detectable probe is attached to an oligonucleotide that hybridizes to a portion of either the forward quenching primer or the reverse quenching primer, and the primer to which the oligonucleotide hybridizes further comprises a quencher that quenches the signal emitted by the detectable probe. In some embodiments, the detectable probe is attached to an oligonucleotide that hybridizes to a portion of either the forward quenching primer or the reverse quenching primer, and the oligonucleotide further comprises a quencher that quenches the signal emitted by the detectable probe.

In some embodiments, the detecting step comprises determining the quantitation cycle (Cq) for the first target nucleic acid amplicon and the second target nucleic acid amplicon. In some embodiments, the detecting step comprises quantitating the amount of fluorescent signal emitted by the fluorescent DNA intercalator and the amount of signal from the detectable probe.

BRIEF DESCRIPTION OF THE DRAWINGS

FIG. 1. General approach for producing a control assay that can be run concurrently with an assay for a gene of interest.

FIG. 7. Schematic for product mediated quenched assay using a detectable probe attached to a primer. In this approach, a forward primer that binds to a nucleic acid sequence of interest comprises quenchers (BHQ1) for quenching the intercalating dye and further comprises a detectable probe that is a fluorophore (Q705). An oligonucleotide that hybridizes to a portion of the forward primer comprises a quencher (BHQ3) that is compatible with the detectable probe Q705. Primer binding and extension results in the dissociation of the forward primer and primer binding oligonucleotide. This dissociation, coupled with the primer incorporation into the final PCR product, results in quenching of the intercalating dye by the BHQ1 quencher and emission of the detectable probe fluorophore Q705.

DETAILED DESCRIPTION OF THE INVENTION

I. Introduction

Figure 2A:
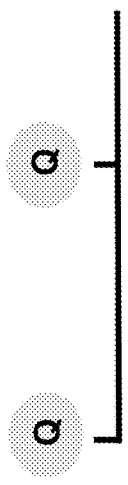
FIG. 2A-2B. (A) Fluorescence quenching primer design. In this exemplary design, the primer contains 2 quenchers: 1 quencher at the 5' end of the primer, and one quencher near the 3' end of the primer (within 7 bases of the 3' end). (B) PCR reaction product for a control nucleic acid, in which the quenchers from the fluorescence quenching primer are incorporated into the PCR reaction product and DNA intercalator is bound to the PCR reaction product.

The present disclosure relates to compositions and methods for reducing fluorescent emission from a specific product within a PCR reaction. Fluorescent dyes that bind to double-stranded DNA are commonly used in qPCR to generate a signal when the PCR reaction generates a product. An example of one such molecule is SYBR®Green. SYBR® Green binds to double-stranded DNA generated during a PCR reaction. SYBR® Green that is bound to a PCR product becomes fluorescent when excited with the appropriate wavelength of light, allowing for real-time amplification of a target of interest as it is amplified. Although SYBR® Green assays have the advantage of not requiring costly hydrolysis probes to be detected, it is difficult to assess more than one product within the same reaction, thus precluding the use of normalizing or control assays to be run concurrently within the same reaction well.

In one aspect, the present disclosure provides compositions, kits, and methods that allow for simultaneous amplification of a control reaction within the same well as a target assay that uses an intercalating dye for generating signal. As described herein, the compositions and methods of the present disclosure provide for the specific quenching of at least a portion of the signal that is emitted by the double-stranded DNA binding dye (i.e., fluorescent DNA intercalator) binding a control PCR product without quenching double-stranded DNA binding dye signal that is emitted from the target PCR product. In some embodiments, the control assay comprises a detectable probe that emits a signal that is distinguishable from the intercalating dye signal, and which can be detected for monitoring the reaction and determining whether the amplification reaction occurred appropriately.

In another aspect, the present disclosure provides compositions, kits, and methods that allow for simultaneous amplification of two different target nucleic acids within the same well, in which one target is detected using an intercalating dye and the other target is detected using a detectable probe that emits a signal that is distinguishable from the intercalating dye signal.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, a "target nucleic acid" refers to a polynucleotide sequence to be detected. In some embodiments, the target is a gene or a portion of a gene. In some embodiments, a target is a polynucleotide sequence (e.g., a gene or a portion of a gene) having a mutation that is associated with a disease such as a cancer. In some embodiments, the target is a polynucleotide sequence having a rare mutation that is associated with a disease such as a cancer.

As used herein, "nucleic acid" refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole.

As used herein, a "fluorescent DNA intercalator" refers to a small molecule that reversibly binds to or inserts between bases of double-stranded nucleic acid (e.g., double-stranded DNA). The fluorescent DNA intercalator emits a fluorescent signal when bound to the double-stranded nucleic acid and produces less or no signal when not bound to double-stranded nucleic acid. Examples of fluorescent DNA intercalators include, but are not limited to, SYBR® Green I, SYBR®Green II, SYBR® Gold, YOYO®, YO-PRO™, TOTO®, PicoGreen®, and EvaGreen®.

As used herein, a "quencher" refers to a compound (e.g., a small molecule dye) that quenches a signal emitted from a fluorescent compound, e.g., a fluorescent DNA intercalator or a fluorescent detectable probe. In some embodiments, the quencher absorbs excitation energy from the fluorescent compound (e.g., fluorescent DNA intercalator or fluorescent detectable probe) and dissipates the energy that is absorbed from the fluorescent compound as heat.

As used herein, a "primer" refers to a polynucleotide sequence that hybridizes to a sequence on a target nucleic acid or control nucleic acid and serves as a point of initiation of nucleic acid synthesis. Primers can be of a variety of lengths. In some embodiments, a primer is less than 100 nucleotides in length, e.g., from about 10 to about 50, from about 15 to about 40, from about 15 to about 30, from about 20 to about 80, or from about 20 to about 60 nucleotides in length. The length and sequences of primers for use in an amplification reaction (e.g., PCR) can be designed based on principles known to those of skill in the art; see, e.g., PCR Protocols: A Guide to Methods and Applications, Innis et al., eds, 1990. In some embodiments, a primer comprises one or more modified or non-natural nucleotide bases.

As used herein, a "quenching primer" refers to a primer that comprises one or more quenchers attached to it. In some embodiments, a quenching primer comprises two or more quenchers attached, e.g., a first quencher attached at or near the 5' end of the primer and a second quencher attached at or near the 3' end of the primer.

A nucleic acid, or portion thereof, "hybridizes" to another nucleic acid under conditions such that non-specific hybridization is minimal at a defined temperature in a physiological buffer. In some cases, a nucleic acid, or portion thereof, hybridizes to a conserved sequence shared among a group of target nucleic acids. In some cases, a primer, or portion thereof, can hybridize to a primer binding site if there are at least about 6, 7, 8, 9, 10, 11, 12, 13, 14, 15, 16, 17, 18, 19, 20, 21, 22, 23, 24, 25, 26, 27, 28, 29, or 30 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 13, 14, 15, 16, 17, 18, 19, 20, 25, or 30 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C., e.g., about 45° C. to about 60° C., e.g., about 55° C.-59° C. In some embodiments, the defined temperature at which specific hybridization occurs is about 5° C. below the calculated melting temperature of the primers.

The term "amplification reaction," as used herein, refers to any in vitro means for multiplying the copies of a target sequence of nucleic acid in a linear or exponential manner. Such methods include but are not limited to polymerase chain reaction (PCR); real-time PCR; DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); or loop-mediated isothermal amplification (LAMP), as well as others known to those of skill in the art.

The term "amplifying," as used herein, refers to a step of submitting a solution (e.g., in a reaction well) to conditions sufficient to allow for amplification of a polynucleotide to yield an amplification product or "amplicon." Components of an amplification reaction include, e.g., primers, a polynucleotide template, polymerase, nucleotides, and the like. The term amplifying typically refers to an exponential increase in target (or control) nucleic acid. However, as used herein, the term amplifying can also refer to linear increases in the numbers of a particular target sequence (or control sequence) of nucleic acid, such as is obtained with cycle sequencing. In an exemplary embodiment, amplifying refers to PCR amplification using a first and a second amplification primer.

The term "polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

III. Compositions for Normalizing Quantitative PCR and Performing Multiplexed Quantitative PCR In one aspect, compositions (e.g., reaction mixtures) for use in an amplification reaction such as qPCR are provided. In some embodiments, the compositions can be used for normalizing an amplification (e.g., qPCR amplification) to a control. In some embodiments, the compositions can be used for performing a multiplexed amplification reaction (e.g., multiplexed qPCR) in the same partition (e.g., in the same reaction well).

In some embodiments, a composition for normalizing an amplification comprises a set of fluorescence quenching primers that specifically bind to a control nucleic acid, the set comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the control nucleic acid; and a detectable probe that specifically associates with the control nucleic acid. In some embodiments, the detectable probe directly binds to the control nucleic acid. In some embodiments, the detectable probe is attached to an oligonucleotide, e.g., to one or both of the quenching primers that specifically bind to the control nucleic acid or to an oligonucleotide that hybridizes to a portion of either the forward quenching primer or the reverse quenching primer.

In some embodiments, a composition for normalizing an amplification comprises a set of fluorescence quenching primers that specifically bind to a control nucleic acid, the set comprising a forward quenching primer and a reverse quenching primer, wherein each of the forward quenching primer and the reverse quenching primer comprises a first quencher at or near the 5' end of the primer and a second quencher near the 3' end of the primer; and a detectable probe that specifically associates with the control nucleic acid.

In some embodiments, a composition for normalizing an amplification comprises:
 a set of fluorescence quenching primers that specifically bind to a control nucleic acid, the set comprising a forward quenching primer and a reverse quenching primer, wherein each of the forward quenching primer and the reverse quenching primer comprises a first quencher at or near the 5' end of the primer and a second quencher near the 3' end of the primer;
 a detectable probe that specifically associates with the control nucleic acid; and
 the control nucleic acid, wherein the control nucleic acid comprises a forward primer binding site to which the forward quenching primer binds, a probe binding site to which the probe binds, and a reverse primer binding site to which the reverse quenching primer binds.

In some embodiments, a composition for performing a multiplexed amplification reaction of a first target nucleic acid and a second target nucleic acid comprises a primer set that is specific for the second target nucleic acid, the primer set comprising a forward quenching primer and a reverse quenching primer that specifically bind to the second target nucleic acid, wherein each of the forward quenching primer and the reverse quenching primer comprises two or more quenchers and wherein the two or more quenchers are positioned within the primer such that the quenchers quench all or substantially all of the fluorescence from an amplification product of the second target nucleic acid; and a detectable probe that specifically associates with the second target nucleic acid.

In some embodiments, a composition for performing a multiplexed amplification reaction of a first target nucleic acid and a second target nucleic acid comprises a primer set that is specific for the second target nucleic acid, the primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer; and a detectable probe that specifically associates with the second target nucleic acid.

In some embodiments, a composition for performing a multiplexed amplification reaction comprises:
 a first target nucleic acid-specific primer set comprising a first target nucleic acid-specific forward primer and a first target nucleic acid-specific reverse primer;
 a second target nucleic acid-specific primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer; and
 a detectable probe that specifically associates with the second target nucleic acid.

In some embodiments, the compositions further comprise a fluorescent DNA intercalator. In some embodiments, the compositions further comprise one or more additional reagents (e.g., primers for target nucleic acids and/or amplification reagents) as disclosed herein.

Control Nucleic Acids

In some embodiments, the compositions (e.g., reaction mixtures) disclosed herein comprise a control nucleic acid. In some embodiments, the control nucleic acid comprises an artificial sequence that does not have significant sequence similarity to any known nucleic acid sequence (e.g., to any nucleic acid sequence of any publicly available nucleic acid database). Methods of generating artificial nucleic acid sequences are described in the art. See, e.g., Caballero et al., *Nucleic Acids Res,* 2014, 42(12):e99. In some embodiments, the control nucleic acid comprises a sequence as disclosed in the Examples section below or is substantially identical to a sequence as disclosed in the Examples section below.

The control nucleic acid may be single stranded or double stranded, or may contain portions of both double stranded and single stranded sequences. For example, the nucleic acid sequence may be genomic DNA, cDNA, mRNA, or a combination or hybrid of DNA and RNA.

Fluorescence Quenching Primers

In some embodiments, the composition comprises a set of fluorescence quenching primers that comprises a forward quenching primer and a reverse quenching primer. In some embodiments, the fluorescence quenching primers specifically bind to a control nucleic acid, e.g., as described above. In some embodiments, the fluorescence quenching primers specifically bind to a second target nucleic acid, e.g., as described above. Methods for designing amplification primers that specifically bind to a sequence of interest (e.g., a control nucleic acid) are disclosed in the art. See, e.g., Thornton et al., *Biochem. Mol. Biol. Educ.,* 2011, 39:145-154.

In some embodiments, a quenching primer (e.g., a forward quenching primer and/or a reverse quenching primer) has a length of at least 15 nucleotides, e.g., at least 20, at least 25, at least 30, at least 35, at least 40, at least 45, or at least 50 nucleotides. In some embodiments, a quenching primer (e.g., a forward quenching primer and/or a reverse quenching primer) has a length of about 15-100 nucleotides, e.g., about 20-80, about 15-50, about 20-30, or about 15-30 nucleotides.

In some embodiments, a quenching primer (e.g., a forward quenching primer and/or a reverse quenching primer) comprises at least two quenchers. In some embodiments, a quenching primer has more than two quenchers, e.g., has 3, 4, 5, 6, 7, 8, 9, or 10 quenchers. The number of quenchers used in a quenching primer can vary depending upon the length of the primer. In some embodiments, the quenchers are positioned within the primer such that the quenchers quench all or substantially all of the fluorescence from an amplification product (e.g., an amplification product of the control nucleic acid or an amplification product of the second target nucleic acid). In some embodiments, the distance between quenchers on a primer does not exceed the Förster radius of the fluorophore that is quenched by the quencher. In some embodiments, a quenching primer comprises a sufficient number of quenchers such that the quenchers are no more than 30 bases apart, e.g., no more than 25 bases apart, or no more than 20 bases apart, throughout the length of the primer. In some embodiments, each of the quenchers in a quenching primer is the same quencher (e.g., each quencher in the primer is a BHQ-1 dye). In some embodiments, each of the quenchers in the set of quenching primers is the same quencher (e.g., each quencher in the forward quenching primer is a BHQ-1 dye and each quencher in the reverse quenching primer is a BHQ-1 dye). In some embodiments, a quenching primer comprises two or more quenchers that quench the same fluorescent DNA intercalator and further comprises one or more quenchers that quench a fluorescent detectable probe, wherein the fluorescent DNA intercalator and the detectable probe have distinguishable emission spectra and are quenched by different quenchers.

In some embodiments, the quencher is a small molecule dye that absorbs excitation energy from a fluorophore (also referred to in the art as a "dark quencher"). Quenchers are described in the art. Exemplary quenchers include, but are not limited to, Black Hole Quencher® (BHQ®) dyes (e.g., BHQ®-0, BHQ®-1, BHQ®-2, and BHQ®-3; LGC Biosearch Technologies, Petaluma, Calif.), Iowa Black® Dark Quenchers (e.g., Iowa Black® FQ and Iowa Black® RQ; Integrated DNA Technologies, Inc., Skokie, Ill.), DABCYL™ QXL™ Quenchers (AnaSpec, Inc. Fremont, Calif.), IRDye® QC-1 (LI-COR Biosciences, Lincoln, Nebr.), and the quenchers described in WO 2001/086001 and US 2005/0164225. A person of ordinary skill in the art will recognize that the choice of quencher will depend upon the fluorescent DNA intercalator being used, and will readily be able to determine a suitable quencher for quenching the fluorescence of the fluorescent DNA intercalator. For example, if the fluorescent DNA intercalator is SYBR® Green I, which emits at 520 nm, suitable quenchers include, but are not limited to, BHQ®-0, BHQ®-1, or Iowa Black® FQ.

In some embodiments, the first quencher is attached at or near the 5' end of the primer. As used herein, a quencher is "near" the end of the primer if it is within 10 bases from the end of the primer. In some embodiments, the first quencher is attached within 1-10 bases from the 5' end of the primer, e.g., within 1-8 bases, within 1-5 bases, within 5-10 bases, or within 2-8 bases from the 5' end of the primer. In some embodiments, the first quencher is about 1, 2, 3, 4, 5, 6, 7, 8, 9, or 10 bases away from the 5' end of the primer. In some embodiments, the first quencher is at the 5' end of the primer.

In some embodiments, the second quencher is attached near the 3' end of the primer. In some embodiments, the second quencher is attached at least 1 base away from the 3' end of the primer, e.g., at least 2 bases, at least 3 bases, at least 4 bases, or at least 5 bases away from the 3' end of the primer. In some embodiments, the second quencher is attached within 5-10 bases from the 3' end, e.g., within 5-8 bases from the 3' end of the primer. In some embodiments, the first quencher is about 2, 3, 4, 5, 6, 7, 8, 9, or 10 bases away from the 5' end of the primer.

Methods of attaching quenchers to a polynucleotide sequence are described in the art. See, e.g., WO 2001/086001 and US 2005/0164225. In some embodiments, the quencher is covalently attached to the primer.

DNA Intercalators

In some embodiments, the composition further comprises a fluorescent DNA intercalator. Fluorescent DNA intercalators are small molecules that fluoresce when intercalated in or bound to double stranded nucleic acids. Typically, the level of fluorescence that is emitted by a fluorescent DNA intercalator is significantly higher when the intercalator is intercalated in or bound to the double stranded nucleic acid, as compared to the basal level of fluorescence when unbound. In some embodiments, the fluorescent DNA intercalator exhibits a very low level of fluorescence when unbound to double stranded nucleic acid.

Exemplary fluorescent DNA intercalators include, but are not limited to, 9-aminoacridine, ethidium bromide, a phenanthridine dye, green fluorescent nucleic acid dye EvaGreen®, 2-[bis[3-(dimethylamino)propyl]amino]-4-[(3-methyl-2(3H)-benzothiazolylidene)methyl]-1-phenylquinolinium PicoGreen® (P-7581, Molecular Probes), propidium iodide (P-4170, Sigma), acridine orange (A-6014, Sigma), thiazole orange, oxazole yellow, 7-aminoactinomycin D (A-1310, Molecular Probes), cyanine dyes (e.g., TOTO®, YOYO®, BOBO®, and POPO®), SYTO®, SYBR® Green I (U.S. Pat. No. 5,436,134: N',N'-dimethyl-N-[4-[(E)-(3-methyl-1,3-benzothiazol-2-ylidene)methyl]-1-phenylquinolin-1-ium-2-yl]-N-propylpropane-1,3-diamine), SYBR® Green II (U.S. Pat. No. 5,658,751), SYBR® DX, OliGreen®, CyQuant® GR, SYTOX® Green, SYTO®9, SYTO®10, SYTO®17, SYBR®14, FUN®-1, DEAD™ Red, hexidium iodide, dihydroethidium, ethidium homodimer, 9-amino-6-chloro-2-methoxyacridine, DAPI, DIPI, indole dye, imidazole dye, hydroxystilbamidine (FluoroGold™), LDS 751 (U.S. Pat. No. 6,210,885), and the dyes described in dyes described in Georghiou, *Photochemistry and Photobiology*, 26:59-68, Pergamon Press (1977); Kubota, et al., *Biophys. Chem.*, 6:279-284 (1977); Genest, et al., *Nucleic Acids Res.*, 13:2603-2615 (1985); Asseline, *EMBO* 1, 3: 795-800 (1984); Richardson, et. al., U.S. Pat. No. 4,257,774; and Letsinger et. al., U.S. Pat. No. 4,547,569. In some embodiments, the fluorescent DNA intercalator is SYBR® Green I, EvaGreen®, PicoGreen®, ethidium bromide, unsymmetrical cyanine dye 2-[N-(3-dimethylaminopropyl)-N-propylamino]-4-[2,3-dihydro-3-methyl-(benzo-1,3-thiazol-2-yl)-methylidene]-1-phenyl-quinolinium SYBR® Gold, 1'-(4,4,7,7-Tetramethyl-4,7-diazaundecamethylene)-bis-4-(3-methyl-2,3-dihydro-(benzo-1,3-oxazole)-2-methylidene)-quinolinium tetraiodide (YOYO®), 4-[(3-methyl-1,3-benzoxazol-2(3H)-ylidene)methyl]-1-[3-(trimethylammonio)propyl]quinolinium diiodide YO-PRO™, 1'-(4,4,7,7-tetramethyl-4,7-diazaundecamethylene)bis-4-(3-methyl-2,3-dihydro(benzo-1,3-thiazole)-2-methylidene)quinolinium TOTO®, 4-[6-(Benzoxazol-2-yl)-dihydro-3-methyl-2(3H)-benzothiazolylidenemethyl]-1-methylquinolinium iodide (BOXTO™), or 4-[(3-methyl-6-(benzothiazol-2-yl)-2,3-dihydro-(benzo-1,3-thiazole)-2-methylidene)]-1-methyl-pyridinium iodide (BEBO™). In some embodiments, the fluorescent DNA intercalator is SYBR® Green I.

In some embodiments, a detectable probe specifically associates with a nucleic acid sequence to be amplified (e.g., a control nucleic acid or a second target nucleic acid). In some embodiments, a detectable probe specifically binds (i.e., directly binds) to the nucleic acid sequence. In some embodiments, the detectable probe is attached to an oligonucleotide sequence (e.g., a primer) that may or may not bind to the nucleic acid sequence to be amplified, e.g., as detailed below.

In some embodiments, a detectable probe comprises an oligonucleotide sequence that hybridizes to a region of a nucleic acid sequence to be amplified (e.g., a region of a control nucleic acid or a region of a second target nucleic acid). In some embodiments, a detectable probe comprises an oligonucleotide sequence having a length of about 15-100 nucleotides, e.g., about 15-75, 15-50, 18-50, 20-50, 15-30, or 18-30 nucleotides.

In some embodiments, the detectable probe is attached to one or both of the fluorescence quenching primers that specifically bind to a nucleic acid (e.g., a forward quenching primer or a reverse quenching primer as disclosed herein). In some embodiments, the detectable probe is attached to a forward quenching primer. In some embodiments, the detectable probe is attached to a reverse quenching primer. In some embodiments, the detectable probe is attached to both the forward quenching primer and the reverse quenching primer. In some embodiments, wherein the detectable probe is attached to the forward quenching primer or the reverse quenching primer, there is also provided an oligonucleotide that hybridizes to a portion of the forward quenching primer or the reverse quenching primer, the oligonucleotide comprising a quencher that quenches the signal emitted by the detectable probe.

In some embodiments, the detectable probe is attached to an oligonucleotide that hybridizes to a portion of either the forward quenching primer or the reverse quenching primer. In some embodiments, the detectable probe is attached to an oligonucleotide that hybridizes to a portion of either the forward quenching primer or the reverse quenching primer, and the primer to which the oligonucleotide hybridizes further comprises a quencher that quenches the signal emitted by the detectable probe. In some embodiments, the detectable probe is attached to an oligonucleotide that hybridizes to a portion of either the forward quenching primer or the reverse quenching primer, and the oligonucleotide further comprises a quencher that quenches the signal emitted by the detectable probe. In some embodiments, the quencher is located sufficiently close to the detectable probe on the oligonucleotide to quench all or substantially all of the signal emitted by the detectable probe). In some embodiments, the oligonucleotide has a length of about 15-100 nucleotides, e.g., about 15-75, 15-50, 18-50, 20-50, 15-30, or 18-30 nucleotides.

In some embodiments, a detectable probe that associates with an amplification product (e.g., a control nucleic acid amplicon) generates a signal that is detectable in an amplification reaction. In some embodiments, the detectable probe comprises a detectable agent such as a fluorescent agent, phosphorescent agent, chemiluminescent agent, etc. In some embodiments, the detectable probe comprises a fluorescent agent. Fluorescent agents can include a variety of organic and/or inorganic small molecules or a variety of fluorescent proteins and derivatives thereof. In some embodiments, the agent is a fluorophore. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); and Wang et al., *Anal. Chem.* 67: 1197-1203 (1995). Non-limiting examples of fluorophores include cyanines (e.g., 1,1'-bis(3-hydroxypropyl)-3,3,3',3'-tetramethylindocarbocyanine (Cy3™), 1,1'-bis(3-hydroxypropyl)-3,3,3',3'-tetramethylindodicarbocyanine (Cy5™)), indocarbocyanines (e.g., Quasar® 570, Quasar® 670, and Quasar® 705) fluoresceins (e.g., 5'-carboxyfluorescein (FAM™,), 6-carboxyfluorescein (6-FAM™,), 5- and 6-carboxyfluorescein (5,6-FAM™,), 2'-chloro-7'phenyl-1,4-dichloro-6-carboxy-fluorescein (VIC™,), 6-carboxy-4'-, 5'-dichloro-2'-, 7'-dimethoxy-fluorescein (JOE™), 4,7,2',4',5',7'-hexachloro-6-carboxy-fluorescein (HEX™) 4,7,2',7'-tetrachloro-6-carboxy-fluorescein (TET™), 2'-chloro-5'-fluoro-7',8'-benzo-1,4-dichloro-6-carboxyfluorescein (NED™), Oregon Green™), and Alexa™ 488), rhodamines (e.g., N,N,N',N'-tetramethyl-6-carboxyrhodamine (TAMRA™) and 5- and 6-carboxy-X-rhodamine (ROX™)), tetramethyl rhodamine, and tetramethyl rhodamine isothiocyanate (TRITC™)), eosin, coumarins, pyrenes, tetrapyrroles, arylmethines, and oxazines. In some embodiments, the detectable probe comprises a fluorescent dye selected from the group consisting of Cy3™ Cy5™, FAM™, HEX™, JOE™ QUASAR®, rhodamine, ROX™, TAMRA™, TET™, sulforhodamine 101 acid chloride (Texas Red™) TYE™, and VIC™.

In some embodiments, the detectable probe comprises a fluorescent dye having an emission spectrum that is distinguishable from the emission spectrum of the fluorescent DNA intercalator. A person of ordinary skill in the art can readily identify the excitation and emission spectra for fluorescent DNA intercalators and fluorescent dyes of the detectable probe and identify fluorescent DNA intercalators and fluorescent dyes that produce distinguishable signals, e.g., when using an appropriate fluorescence filter. In some embodiments, the excitation and emission spectra of the fluorescent DNA intercalator do not substantially overlap with the excitation and emission spectra of the fluorescent dye of the detectable probe.

In some embodiments, the detectable probe is a hydrolysis probe (also referred to as a TaqMan™ probe). Typically, a hydrolysis probe is an oligonucleotide probe having a fluorophore covalently attached to the 5' end of the oligonucleotide and a quencher at the 3' end. The TaqMan™ probe relies on the 5'-3' exonuclease activity of DNA polymerase to specifically cleave the probe during hybridization to the complementary target sequence. Cleavage of the probe generates an increase in the fluorescence intensity of the reporter dye.

In some embodiments, the detectable probe is a molecular beacon probe. Typically, a molecular beacon probe is an oligonucleotide hybridization probe that can form hairpin structures. On one end of the hybridization probe (either the 5' or 3' end), there is a donor fluorophore, and on the other end, an acceptor moiety. In some instances, this acceptor moiety is a quencher that absorbs energy released by the donor, but then does not itself fluoresce. See, Tyagi and Kramer, Nature Biotechnol. 14: 303-306 (1996). Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce.

Additional Amplification Reaction Components

In some embodiments, the compositions further comprise one or more additional reagents, e.g., amplification reagents. In some embodiments, the composition further comprises one or more of buffers, salts, nucleotides, stabilizers, primers, polymerases, or nuclease-free water.

In some embodiments, the composition comprises a DNA polymerase. DNA polymerases for use in the compositions and methods disclosed herein can be any polymerase capable of replicating a DNA molecule. In some embodiments, the DNA polymerase is a thermostable polymerase. Thermostable polymerases are isolated from a wide variety of thermophilic bacteria, such as *Thermus aquaticus* (Taq), *Pyrococcus furiosus* (Pfu), *Pyrococcus woesei* (Pwo), *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), as well as other species. DNA polymerases are known in the art and are commercially available. In some embodiments, the DNA polymerase is Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, or an active mutant, variant, or derivative thereof. In some embodiments, the DNA polymerase is Taq DNA polymerase. In some embodiments, the DNA polymerase is a high fidelity DNA polymerase (e.g., iProof™ High-Fidelity DNA Polymerase, Phusion® High-Fidelity DNA polymerase, Q5® High-Fidelity DNA polymerase, Platinum® Taq High Fidelity DNA polymerase, Accura® High-Fidelity Polymerase). In some embodiments, the DNA polymerase is a fast-start or hot-start polymerase (e.g., FastStart™ Taq DNA polymerase, FastStart™ High Fidelity DNA polymerase, or iTaq™ DNA polymerase).

In some embodiments, the composition comprises nucleotides. Nucleotides for use in the compositions and methods disclosed herein can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). In some embodiments, the nucleotides are deoxynucleoside triphosphates ("dNTPs," e.g., dATP, dCTP, dGTP, dTTP, dITP, dUTP, α-thio-dNITs, biotin-dUTP, fluorescein-dUTP, digoxigenin-dUTP, or 7-deaza-dGTP). dNTPs are well-known in the art and are commercially available. Nucleotides can be present in any suitable concentration. In some embodiments, the nucleotides are present in an amount from about 1 µM to about 1000 µM, e.g., from about 10 µM to about 750 µM, or from about 100 µM to about 500 µM.

In some embodiments, the composition comprises one or more buffers or salts. A wide variety of buffers and salt solutions and modified buffers are known in the art. For example, in some embodiments, the buffer is TRIS, TRICINE, BIS-TRICINE, HEPES, MOPS, TES, TAPS, PIPES, or CAPS. In some embodiments, the salt is potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, or lithium acetate.

Buffers and/or salts can be present in any suitable concentration. In some embodiments, the buffer is present in an amount from about 0.1 mM to about 1000 mM, e.g., from about 1 mM to about 500 mM or from about 5 mM to about 250 mM. In some embodiments, the salt is present in an amount from about 0.01 mM to about 1000 mM, e.g., from about 0.1 mM to about 500 mM or from about 1 mM to about 100 mM. In some embodiments, the composition comprises a salt (e.g., potassium chloride or magnesium chloride) at a concentration of about 10 mM to about 100 mM.

In some embodiments, the composition comprises one or more stabilizers. Stabilizers for use in the compositions and methods disclosed herein include, but are not limited to, polyol (glycerol, threitol, etc.), a polyether including cyclic polyethers, polyethylene glycol, organic or inorganic salts, such as ammonium sulfate, sodium sulfate, sodium molybdate, sodium tungstate, organic sulfonate, etc., sugars, polyalcohols, amino acids, peptides or carboxylic acids, mannitol, glycerol, reduced glutathione, superoxide dismutase, bovine serum albumin (BSA) or gelatine, spermidine, dithiothreitol (or mercaptoethanol), and/or detergents such as TRITON® X-100 [Octophenol(ethyleneglycolether)], THESIT® [Polyoxyethylene 9 lauryl ether (Polidocanol Cie E9)], TWEEN® (Polyoxyethylenesorbitan monolaurate 20, NP40) and BRIJ®-35 (Polyoxyethylene23 lauryl ether).

In some embodiments, a composition as disclosed herein is in a liquid form, e.g., a solution. In some embodiments, a composition as disclosed herein is in lyophilized form. In some embodiments, a composition that is in lyophilized form is reconstituted by the end user of the composition.

IV. Methods for Normalizing Quantitative PCR

In another aspect, methods for normalizing a qPCR amplification to a control are provided. In some embodiments, the method comprises:

combining a target nucleic acid and a control nucleic acid with (i) a fluorescent DNA intercalator, (ii) a set of target nucleic acid-specific primers comprising a target nucleic acid-specific forward primer and a target nucleic acid-specific reverse primer, (iii) a detectable probe that specifically associates with the control nucleic acid, and (iv) a set of fluorescence quenching primers that specifically bind to a control nucleic acid comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the control nucleic acid, thereby forming a reaction mixture;

incubating the reaction mixture under conditions suitable to generate a target nucleic acid amplicon and a control nucleic acid amplicon, wherein the fluorescent DNA intercalator binds to both the target nucleic acid amplicon and the control nucleic acid amplicon and wherein the control nucleic acid amplicon that is generated comprises a plurality of quenchers incorporated into the amplicon;

exciting the fluorescent DNA intercalator, wherein the quenchers that are incorporated into the control nucleic acid amplicon quench at least a portion of the fluorescence emitted by the fluorescent DNA intercalator bound to the control nucleic acid amplicon; and detecting the target nucleic acid amplicon and the control nucleic acid amplicon, wherein the target nucleic acid amplicon is detected by detecting the fluorescent signal emitted by the fluorescent DNA intercalator and wherein the control nucleic acid amplicon is detected by detecting the detectable probe.

In some embodiments, the method comprises:

combining a target nucleic acid and a control nucleic acid with (i) a fluorescent DNA intercalator, (ii) a set of target nucleic acid-specific primers comprising a target nucleic acid-specific forward primer and a target nucleic acid-specific reverse primer, (iii) a detectable probe that specifically associates with the control nucleic acid, and (iv) a set of fluorescence quenching primers that specifically bind to a control nucleic acid comprising a forward quenching primer and a reverse quenching primer, wherein each of the forward quenching primer and the reverse quenching primer comprises a first quencher at or near the 5' end of the primer and a second quencher near the 3' end of the primer, thereby forming a reaction mixture;

incubating the reaction mixture under conditions suitable to generate a target nucleic acid amplicon and a control nucleic acid amplicon, wherein the fluorescent DNA intercalator binds to both the target nucleic acid amplicon and the control nucleic acid amplicon and wherein the control nucleic acid amplicon that is generated comprises a plurality of quenchers incorporated into the amplicon;

exciting the fluorescent DNA intercalator, wherein the quenchers that are incorporated into the control nucleic acid amplicon quench at least a portion of the fluorescence emitted by the fluorescent DNA intercalator bound to the control nucleic acid amplicon; and detecting the target nucleic acid amplicon and the control nucleic acid amplicon, wherein the target nucleic acid amplicon is detected by detecting the fluorescent signal emitted by the fluorescent DNA intercalator and wherein the control nucleic acid amplicon is detected by detecting the detectable probe.

Target Nucleic Acids

The target nucleic acid sequence may be any gene, non-coding genomic region, or sequence of interest. In some embodiments, the target nucleic acid sequence is a gene or sequence that is associated with a disease (e.g., a cancer, a neuromuscular disease, a cardiovascular disease, a developmental disease, or a metabolic disease). In some embodiments, the target nucleic acid sequence is a gene or sequence that is associated with a cancer, including but not limited to bladder cancer, brain cancer, breast cancer, cervical cancer, colorectal cancer, endometrial cancer, esophageal cancer, gastric cancer, head and neck cancer, kidney cancer, leukemia, liver cancer, lung cancer, lymphoma, melanoma, ovarian cancer, pancreatic cancer, prostate cancer, or thyroid cancer. In some embodiments, the target nucleic acid sequence is a gene or sequence that is associated with a disease, including but not limited to autism spectrum disorders, cardiomyopathy, ciliopathies, congenital disorders of glyosylation, congenital myasthenic syndromes, epilepsy and seizure disorders, eye disorders, glycogen storage disorders, hereditary cancer syndrome, hereditary periodic fever syndromes, inflammatory bowel disease, lysosomal storage disorders, multiple epiphyseal dysplasia, neuromuscular disorders, Noonan Syndrome and related disorders, perioxisome biogenesis disorders, or skeletal dysplasia.

The target nucleic acid may be single stranded or double stranded, or may contain portions of both double stranded and single stranded sequences. For example, the nucleic acid sequences may be genomic DNA, cDNA, mRNA, or a combination or hybrid of DNA and RNA.

In some embodiments, the target nucleic acid is obtained from a sample such as a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc.

In some embodiments, prior to the combining step, a sample comprising the target nucleic acid is subjected to one or more processing steps. For example, the sample can be purified, fractionated, enriched or filtered. In some embodiments, the nucleic acids in the sample are processed by fragmentation to produce fragments of one or more specific sizes, e.g., by mechanical means such as ultrasonic cleavage, acoustic shearing, needle shearing, or sonication, by chemical methods, or by enzymatic methods such as using endonucleases. In some embodiments, fragmented nucleic acids (e.g., target nucleic acids) are subjected to a size selection step to obtain nucleic acid fragments having a certain size or range of sizes. Methods of size selection are known in the art. For example, fragmented nucleic acids can be separated by gel electrophoresis, spin columns, or paramagnetic beads.

Reaction Mixtures

The target nucleic acid(s) is combined in a reaction mixture with a control nucleic acid, a detectable probe that specifically associates with the control nucleic acid, and a set of fluorescence quenching primers that specifically bind to a control nucleic acid (e.g., as in a composition as disclosed in Section III above) as well as a fluorescent DNA intercalator and a set of target nucleic acid-specific primers comprising a target nucleic acid-specific forward primer and a target nucleic acid-specific reverse primer. In some embodiments, wherein the detectable probe is attached to a fluorescence quenching primer, the reaction mixture further comprises an oligonucleotide that hybridizes to a portion of the primer, the oligonucleotide comprising a quencher that quenches the signal emitted by the detectable probe.

In some embodiments, a target nucleic acid-specific primer (e.g., a forward target nucleic acid-specific primer and/or a reverse target nucleic acid-specific primer) has a length of at least 15 nucleotides, e.g., at least 20, at least 25, at least 30, at least 35, at least 40, at least 45, or at least 50 nucleotides. In some embodiments, a target nucleic acid-specific primer (e.g., a forward target nucleic acid-specific primer and/or a reverse target nucleic acid-specific primer) has a length of about 15-100 nucleotides, e.g., about 20-80, about 15-50, about 20-30, or about 15-30 nucleotides.

In some embodiments, the reaction mixture further comprises one or more additional amplification reagents (e.g., as described in Section III above), such as but not limited to one or more of buffers, salts, nucleotides, stabilizers, primers, polymerases, or nuclease-free water.

Amplification

In some embodiments, the reaction mixture is incubated under conditions suitable to generate a target nucleic acid amplicon and a control nucleic acid amplicon. In some embodiments, the target nucleic acid amplicon and the control nucleic acid are amplified by PCR amplification. Other amplification methods are also known in the art.

Generally, in PCR amplification nucleic acids are amplified by subjecting a reaction mixture to cycles of: (i) nucleic acid denaturation, (ii) oligonucleotide primer annealization, and (iii) nucleic acid polymerization (extension). Preferred reaction conditions for amplification comprise thermocycling, i.e., alternating the temperature of the reaction mixture to facilitate each of the steps of the PCR cycle. PCR is typically extended through multiple cycles of denaturation, annealization and replication, augmented (optionally and preferably) with an initial prolonged denaturation step and a final prolonged extension (polymerization) step. In some embodiments, a PCR reaction can be "two-step PCR," in which the annealing and extension steps are combined into a single step.

Suitable PCR amplification conditions can be readily determined by a person of ordinary skill in the art, and may vary depending on factors such as the amount and composition of the target(s) to be amplified, the composition of primers used, and the composition of other amplification reagents such as the DNA polymerase. Typically, thermocycling occurs within a temperature range of between about 23° C. to about 100° C., e.g., between about 37° C. to about 95° C. Nucleic acid denaturation typically occurs between about 90° C. to about 100° C., e.g., at about 94° C. Annealization typically occurs between about 37° C. to about 75° C., e.g., at about 58° C. to about 60° C. Polymerization typically occurs between about 55° C. to about 80° C., e.g., about 72° C. The number of PCR cycles can range, e.g., from about 5 to about 99 cycles, e.g., at least about 10, about 15, about 20, or about 25 cycles.

In some embodiments, the target nucleic acid amplicon that is generated by the amplifying step comprises a fluorescent DNA intercalator that is bound to the target nucleic acid amplicon. In some embodiments, the control nucleic acid amplicon that is generated by the amplifying step comprises a fluorescent DNA intercalator that is bound to the control nucleic acid amplicon and further comprises a plurality of quenchers that are incorporated into the amplicon. Thus, although both the target nucleic acid amplicon and the control nucleic acid amplicon both comprise bound fluorescent DNA intercalator, the control nucleic acid amplicon further comprises quenchers that specifically quench the fluorescence of the fluorescent DNA intercalator bound to the control nucleic acid amplicon due to the close proximity of the quencher and the fluorescent DNA intercalator on the control nucleic acid amplicon.

Excitation and Detection

During amplification, the fluorescent DNA intercalator inserts into the nucleic acid being amplified (e.g., the target nucleic acid amplicon and the control nucleic acid amplicon). Typically, a fluorescent DNA intercalator exhibits much higher fluorescence when bound to DNA than when unbound. Thus, the presence of an amplified nucleic acid can be determined by detecting fluorescence from the DNA intercalator.

As shown in FIGS. 1 and 2, fluorescence from the DNA intercalator can be used to specifically detect the presence of an amplified target nucleic acid because the presence of quenching primers that specifically bind to the control nucleic acid quench at least a portion of the fluorescent signal from the DNA intercalator bound to the control nucleic acid. In contrast, in the absence of quenching primers for the control nucleic acid, fluorescence from the DNA intercalator bound to the control nucleic acid amplicon impedes the specific detection of fluorescence from the DNA intercalator bound to the target nucleic acid, as shown in FIG. 3.

For detecting fluorescence from the DNA intercalator, a suitable wavelength of excitation light is applied to the reaction mixture (e.g., from a light source such as a light-emitting diode, halogen lamp, or laser). In some embodiments, an emission filter is used to allow only specific wavelengths or ranges of wavelengths to be applied to the reaction mixture. The excitation wavelength for the fluorescent DNA intercalator will vary depending upon the composition of the fluorescent DNA intercalator. A person of ordinary skill in the art can readily determine a suitable excitation wavelength and the resulting emission wavelength for the fluorescent DNA intercalator. As a non-limiting example, SYBR Green I has an excitation wavelength of approximately 494 nm and an emission wavelength of approximately 521 nm; in some embodiments, blue light can be used for excitation to result in emission of fluorescence.

In some embodiments, the detecting step also comprises detecting the detectable probe that binds to the control nucleic acid amplicon. The detectable probe may comprise any detectable agent such as a fluorescent agent, phosphorescent agent, or chemiluminescent agent, e.g., as disclosed in Section III above. In some embodiments, the detectable probe comprises a fluorescent agent. In such embodiments, the detectable probe can be any fluorescent agent that is distinguishable from the fluorescent DNA intercalator. In some embodiments, a detectable probe comprising a fluorescent agent is distinguishable from the fluorescent DNA intercalator if an optical filter (e.g., an emission filter) can specifically transmit the emission of one (e.g., specifically transmitting the emission of the fluorescent DNA intercalator) while blocking transmission of the emission of the other (e.g., blocking transmission of the emission of the detectable probe fluorescent agent). In some embodiments, the excitation and emission spectra of the fluorescent DNA intercalator do not overlap with the excitation and emission spectra of the fluorescent dye of the detectable probe. In some embodiments, the excitation and emission spectra of the fluorescent DNA intercalator do not substantially overlap with the excitation and emission spectra of the fluorescent dye of the detectable probe.

In some embodiments, fluorescence can be detected using a detector device equipped with a module to generate excitation light that can be absorbed by a fluorophore, as well as a module to detect light emitted by the fluorophore. Light sources, filters, and devices for exciting fluorophores and detecting fluorescent signals are known in the art. In some embodiments, the fluorescence detection modules or devices are incorporated into an apparatus or device for performing the amplification reaction, e.g., the CFX Real-Time PCR Detection System (Bio-Rad Laboratories, Inc., Hercules, Calif.). Devices and systems for detecting fluorescence are also disclosed in Section VI below.

In some embodiments, the detecting step comprises quantitating the amount of fluorescent signal emitted by the fluorescent DNA intercalator (i.e., the target nucleic acid signal) and/or the amount of signal from the detectable probe (i.e., the control nucleic acid signal). In some embodiments, the detecting step comprises determining the quantitation cycle (Cq) for the target nucleic acid amplicon and the control nucleic acid amplicon. Methods of determining Cq for an amplification reaction are described in the art. See, e.g., US 2016/0210406.

In some embodiments, the method comprises normalizing the target nucleic acid signal to the control nucleic acid signal. In some embodiments, a target nucleic acid signal for a partition or reaction well is normalized to a control nucleic acid signal from the same partition or reaction well. In some embodiments, the step of normalizing a target nucleic acid signal for a particular partition or reaction well comprises detecting a Cq for the control nucleic acid signal for that partition or reaction well, determining whether the Cq for the control nucleic acid signal falls within predetermined Cq boundaries for the assay, and if the Cq for the control nucleic acid signal does not fall within the predetermined Cq boundaries, rejecting the target nucleic acid signal for that partition or reaction well.

V. Methods for Multiplexing Quantitative PCR

In another aspect, method for multiplexing an amplification (e.g., qPCR amplification) of two target nucleic acids in the same partition (e.g., reaction well) are provided. In some embodiments, the method comprises:

combining a sample comprising a first target nucleic acid and a second target nucleic acid with (i) a fluorescent DNA intercalator, (ii) a first target nucleic acid-specific primer set comprising a first target nucleic acid-specific forward primer and a first target nucleic acid-specific reverse primer, (iii) a detectable probe that specifically associates with the second target nucleic acid, and (iv) a second target nucleic acid-specific primer set comprising a forward quenching primer and a reverse quenching primer that specifically bind to the second target nucleic acid, wherein each of the forward quenching primer and the reverse quenching primer comprises two or more quenchers and wherein the two or more quenchers are positioned within the primer such that the quenchers quench all or substantially all of the fluorescence from an amplification product of the second target nucleic acid, thereby forming a reaction mixture;

incubating the reaction mixture under conditions suitable to generate a first target nucleic acid amplicon and a second target nucleic acid amplicon, wherein the fluorescent DNA intercalator binds to both the first target nucleic acid amplicon and the second target nucleic acid amplicon and wherein the second target nucleic acid amplicon that is generated comprises a plurality of quenchers incorporated into the amplicon;

exciting the fluorescent DNA intercalator (e.g., using a light source), wherein the quenchers in the second target nucleic acid amplicon quench at least a portion of the fluorescence emitted by the fluorescent DNA intercalator bound to the second target nucleic acid amplicon; and detecting the first target nucleic acid amplicon and the second target nucleic acid amplicon, wherein the first target nucleic acid amplicon is detected by detecting the fluorescent signal emitted by the fluorescent DNA intercalator and wherein the second target nucleic acid amplicon is detected by detecting the detectable probe.

In some embodiments, the method comprises:

combining a sample comprising a first target nucleic acid and a second target nucleic acid with (i) a fluorescent DNA intercalator, (ii) a first target nucleic acid-specific primer set comprising a first target nucleic acid-specific forward primer and a first target nucleic acid-specific reverse primer, (iii) a detectable probe that specifically associates with the second target nucleic acid, and (iv) a second target nucleic acid-specific primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer, thereby forming a reaction mixture;

incubating the reaction mixture under conditions suitable to generate a first target nucleic acid amplicon and a second target nucleic acid amplicon, wherein the fluorescent DNA intercalator binds to both the first target nucleic acid amplicon and the second target nucleic acid amplicon and wherein the second target nucleic acid amplicon that is generated comprises a plurality of quenchers incorporated into the amplicon;

exciting the fluorescent DNA intercalator (e.g., using a light source), wherein the quenchers in the second target nucleic acid amplicon quench at least a portion of the fluorescence emitted by the fluorescent DNA intercalator bound to the second target nucleic acid amplicon; and detecting the first target nucleic acid amplicon and the second target nucleic acid amplicon, wherein the first target nucleic acid amplicon is detected by detecting the fluorescent signal emitted by the fluorescent DNA intercalator and wherein the second target nucleic acid amplicon is detected by detecting the detectable probe.

In some embodiments, wherein the detectable probe emits a fluorescent signal that is distinguishable from the signal emitted by the fluorescent DNA intercalator, the method further comprises exciting the detectable probe and detecting the fluorescent signal emitted by the detectable probe, e.g., as described in Section IV above.

Each of the first target nucleic acid sequence and the second target nucleic acid sequence may be any gene, non-coding genomic region, or sequence of interest. In some embodiments, each of the first target nucleic acid sequence and the second target nucleic acid sequence is a gene or sequence that is associated with a disease (e.g., a cancer, a neuromuscular disease, a cardiovascular disease, a developmental disease, or a metabolic disease), such as a disease or cancer disclosed in Section IV above. In some embodiments, each of the first target nucleic acid sequence and the second target nucleic acid sequence is a gene or sequence that is associated with the same disease.

Each of the first target nucleic acid and the second target nucleic acid may be single stranded or double stranded, or may contain portions of both double stranded and single stranded sequences. In some embodiments, the first target nucleic acid and/or the second target nucleic acid is genomic DNA, cDNA, mRNA, or a combination or hybrid of DNA and RNA.

The first target nucleic acid and the second target nucleic acid can be obtained from any suitable sample, e.g., a sample as disclosed in Section IV above. In some embodiments, the first target nucleic acid and the second target nucleic acid are obtained from the same sample. In some embodiments, the first target nucleic acid and the second target nucleic acid are obtained from different samples, e.g., samples from different subjects, different cell or tissue samples from the same subject, or samples from the same cell or tissue type from the same subject at different timepoints. In some embodiments, the sample(s) comprising the target nucleic acids is subjected to one or more processing steps, e.g., as disclosed in Section IV above.

In some embodiments, a reaction mixture is formed that comprises the first target nucleic acid, the second target nucleic acid, a first primer set specific for the first target nucleic acid, a second primer set specific for the second target nucleic acid in which the second primer set comprises a forward quenching primer and a reverse quenching primer that specifically bind to the second target nucleic acid, a fluorescent DNA intercalator, and a detectable probe that specifically binds to the second target nucleic acid. In some embodiments, the primer sets, fluorescent DNA intercalator, and detectable probe are as disclosed in Section III or Section IV above. In some embodiments, the reaction mixture further comprises one or more additional amplification reagents (e.g., as described in Section III above), such as but not limited to one or more of buffers, salts, nucleotides, stabilizers, primers, polymerases, or nuclease-free water.

In some embodiments, the reaction mixture is incubated under conditions suitable to generate a first target nucleic acid amplicon and a second target nucleic acid amplicon. In some embodiments, the incubation comprises amplifying the first target nucleic acid amplicon and the second target nucleic acid by PCR amplification, e.g., as disclosed in Section IV above. In some embodiments, the first target nucleic acid amplicon that is generated by the amplifying step comprises a fluorescent DNA intercalator that is bound to the target nucleic acid amplicon. In some embodiments, the second target nucleic acid amplicon that is generated by the amplifying step comprises a fluorescent DNA intercalator that is bound to the amplicon and further comprises a plurality of quenchers that are incorporated into the amplicon.

In some embodiments, the first target nucleic acid amplicon and a second target nucleic acid amplicon are detected as disclosed in Section IV above. In the multiplexing assays disclosed herein, fluorescence from the DNA intercalator can be used to specifically detect the presence of the first target nucleic acid because the presence of quenching primers that specifically bind to the second target nucleic acid quench at least a portion of the fluorescent signal from the DNA intercalator bound to the second target nucleic acid. In some embodiments, the detecting step comprises quantitating the amount of fluorescent signal emitted by the fluorescent DNA intercalator and/or the amount of signal from the detectable probe. In some embodiments, the detecting step comprises determining the quantitation cycle (Cq) for the first target nucleic acid amplicon and a second target nucleic acid amplicon.

VI. Detection Systems

Also provided herein are detection devices and systems for detecting and/or quantitating the amount of fluorescent signal emitted by the fluorescent DNA intercalator and the amount of signal from the detectable probe. In some embodiments, fluorescence can be detected using a detector device equipped with a module to generate excitation light that can be absorbed by a fluorophore, as well as a module to detect light emitted by the fluorophore. Devices and systems for monitoring nucleic acid amplification reactions and detecting fluorescent signal emitted during the amplification reaction are known in the art. See, e.g., U.S. Pat. No. 6,814,934.

Following acquisition of fluorescence detection data, a general purpose computer system (referred to herein as a "host computer") can be used to store and process the data. A computer-executable logic can be employed to perform such functions as subtraction of background signal, assignment of target and/or reference sequences, and quantification of the data. A host computer can be useful for displaying, storing, retrieving, or calculating diagnostic results from the nucleic acid detection; storing, retrieving, or calculating raw data from the nucleic acid detection; or displaying, storing, retrieving, or calculating any sample or patient information useful in the methods of the present invention.

In some embodiments, the host computer or any other computer may be used to quantitate the absolute or relative amount of a target nucleic acid amplicon or to calculate a quantitation cycle (Cq) for a target nucleic acid amplicon and/or a control nucleic acid amplicon.

In some embodiments, the host computer or any other computer may be used to assess uniformity of an assay or determine whether a reaction sample falls within acceptable boundaries of deviation for the assay.

The host computer can be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, can be included. Where the host computer is attached to a network, the connections can be provided via any suitable transport media (e.g., wired, optical, and/or wireless media) and any suitable communication protocol (e.g., TCP/IP); the host computer can include suitable networking hardware (e.g., modem, Ethernet card, WiFi card). The host computer can implement any of a variety of operating systems, including UNIX, Linux, Microsoft Windows, MacOS, or any other operating system.

Computer code for implementing aspects of the present invention can be written in a variety of languages, including PERL, C, C++, Java, JavaScript, VB Script, AWK, or any other scripting or programming language that can be executed on the host computer or that can be compiled to execute on the host computer. Code can also be written or distributed in low level languages such as assembler languages or machine languages.

Scripts or programs incorporating various features of the present invention can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

VII. Solid Supports and Kits

In some embodiments, a composition as disclosed herein is attached to or included within a solid support comprising one or more partitions. In some embodiments, the solid support is an assay plate, e.g., a multiwell assay plate such as a 6-well, 12-well, 24-well, 48-well, or 96-well plate.

In some embodiments, the composition comprises primers (e.g., fluorescence quenching primers), detectable probes, and/or control nucleic acids as described in Section III above. some embodiments, the composition is in a liquid form, e.g., a solution, and the composition is provided within the partitions (e.g., wells) of the solid support (e.g., assay plate). In some embodiments, the composition is in a lyophilized form and the composition is attached to or provided within the partitions (e.g., wells) of the solid support (e.g., assay plate).

In another aspect, kits for normalizing a qPCR amplification or for performing a multiplex reaction in the same reaction well are provided. In some embodiments, the kit comprises:

a set of fluorescence quenching primers that specifically bind to a nucleic acid (e.g., a control nucleic acid or a target nucleic acid), the set comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the nucleic acid; and a detectable probe that specifically associates with the nucleic acid.

In some embodiments, the kit is for normalizing a qPCR amplification. In some embodiments, the kit for normalizing a qPCR amplification comprises a composition as disclosed in Section III above. In some embodiments, the kit comprises:

a set of fluorescence quenching primers that specifically bind to a control nucleic acid, the set comprising a forward quenching primer and a reverse quenching primer, wherein each of the forward quenching primer and the reverse quenching primer comprises a first quencher at or near the 5' end of the primer and a second quencher near the 3' end of the primer;

a detectable probe that specifically associates with the control nucleic acid; and the control nucleic acid, wherein the control nucleic acid comprises a forward primer binding site to which the forward quenching primer binds, a probe binding site to which the probe binds, and a reverse primer binding site to which the reverse quenching primer binds.

In some embodiments, the kit is for performing a multiplex reaction in the same reaction well. In some embodiments, the kit for performing a multiplex reaction comprises a composition as disclosed in Section III above. In some embodiments, the kit comprises:
  a first target nucleic acid-specific primer set comprising a first target nucleic acid-specific forward primer and a first target nucleic acid-specific reverse primer;
  a second target nucleic acid-specific primer set comprising a forward quenching primer and a reverse quenching primer that specifically bind to the second target nucleic acid, wherein each of the forward quenching primer and the reverse quenching primer comprises a first quencher at or near the 5' end of the primer and a second quencher near the 3' end of the primer; and
  a detectable probe that specifically associates with the second target nucleic acid.

In some embodiments, a kit as disclosed herein comprises primers (e.g., fluorescence quenching primers or target-specific primers), detectable probes, and/or control nucleic acids as described in Section III and Section IV above.

In some embodiments, the kit further comprises a fluorescent DNA intercalator, e.g., as described in Section III above. In some embodiments, the fluorescent DNA intercalator is SYBR® Green I, EvaGreen®, PicoGreen®, ethidium bromide, SYBR® Gold, YOYO® YO-PRO™, TOTO®, BOXTO™, or BEBO™. In some embodiments, the fluorescent DNA intercalator is SYBR® Green I or EvaGreen®.

In some embodiments, the kit further comprises one or more additional reagents, e.g., amplification reagents. In some embodiments, the kit further comprises one or more reagents selected from the group consisting of salts, nucleotides, buffers, stabilizers, DNA polymerase, detectable agents, and nuclease-free water. Amplification reagents are described in Section III above.

In some embodiments, the kit comprises a solid support comprising one or more partitions, in which the one or more partitions comprise a composition as disclosed herein. In some embodiments, the solid support comprises a composition that is in a solution form. In some embodiments, the solid support comprises a composition that is in a lyophilized form. In some embodiments, the solid support is a multiwell assay plate, e.g., a 6-well, 12-well, 24-well, 48-well, or 96-well plate.

For kits comprising the composition in lyophilized form, or a solid support comprising the composition in lyophilized form, in some embodiments, the composition is reconstituted by the end user. Thus, in some embodiments, the kit further comprises instructions for reconstituting the lyophilized composition.

In some embodiments, the kit further comprises instructional materials containing directions (i.e., protocols) for the practice of the methods of this disclosure (e.g., instructions for using the kit for normalizing a qPCR assay). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VIII. Examples

The following examples are offered to illustrate, but not to limit, the claimed invention.

Example 1: Generation of Control Assay for Normalizing qPCR

Fluorescent DNA intercalators, such as SYBR Green, are commonly used in real-time quantitation of PCR. However, because fluorescent DNA intercalators bind to any double-stranded nucleic acid sequence in a sample, it is difficult to assess more than one product within the same reaction well. Therefore, qPCR reagents were developed that allow for the use of fluorescent DNA intercalators and the normalization of experimental samples to controls in the same reaction well, thereby allowing for more robust quantitation through qPCR.

FIG. 1 shows an overview of the general approach for producing a control assay that can be run concurrently with an assay for a gene of interest. In this assay, a target nucleic acid ("gene of interest") and a control nucleic acid ("control") are present in a sample. The sample is incubated with primers that are specific to the gene of interest, primers that are specific to the control, and a fluorescent DNA intercalator. PCR amplification is performed, resulting in PCR products for both the gene of interest and the control that have bound fluorescent DNA intercalator (SYBR Green). Excitation with blue light results in emission of fluorescence from the SYBR Green for the gene of interest, but not for the control.

A control assay was developed in which the following artificial DNA sequence having no significant sequence similarity to any publicly available nucleic acid sequence was used as the control DNA sequence:

(SEQ ID NO: 1)
TGGACATTGTCGATCCGCGTGAAAGTTAGGTGGAATCGCATCATAGCC

CCGTTCTAGGCTCTCCGACGGCACTATCTAAGGCTCTGTCAACAAAAC

GTATCCAGTGGTATGCCGTGTATTGTAATG

In this sequence, the primer binding sites are underlined, and the binding site for the detectable probe is italicized. A hydrolysis probe comprising a Quasar 705 fluorescent dye and a BHQ3 quencher was used as the detectable probe.

Figure 2B:
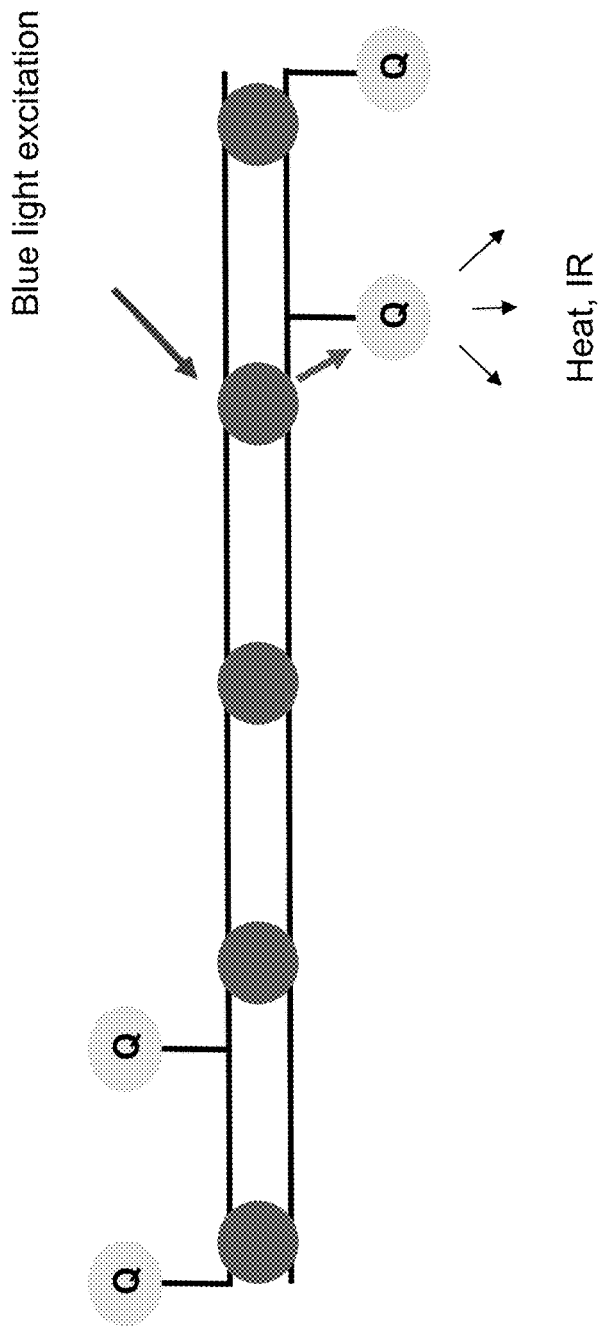

To achieve quenching of the fluorescence in the control PCR product, fluorescence quenching control assay primers were generated. By incorporating quenchers into the primers that are specific for the control nucleic acid, the quenchers become incorporated into the control nucleic acid amplicon during the PCR amplification reaction, and as a result, DNA intercalator adsorption by the control nucleic acid amplicon yields reduced fluorescence due to quenching by the quenchers in the control nucleic acid amplicon. FIG. 2A shows an exemplary design of a fluorescence quenching control primer having two quenchers ("Q"), one at the 5' end of the primer and the other near the 3' end of the primer. Both the forward primer and the reverse primer can have this exemplary design. FIG. 2B shows the resulting PCR amplification product with quenchers ("Q") incorporated into the product and DNA intercalator (green circles) bound to the product. Upon blue light excitation, quenchers that are near bound DNA intercalator absorb the fluorescence and emit the energy as heat. The quenching of at least some of the fluorescence emitted by the DNA intercalator in the control product results in a decreased fluorescent intensity for the quenched assay.

An alternative approach for achieving quenching of fluorescence in a control PCR product is shown in FIG. 7. In this approach, a forward primer that binds to a nucleic acid sequence (e.g., a control nucleic acid) comprises quenchers (BHQ®1) for quenching the intercalating dye and further comprises a detectable probe that is a fluorophore (Q70). An oligonucleotide that hybridizes to a portion of the forward primer comprises a quencher (BHQ®3) that is compatible with the detectable probe Q705. Primer binding and extension results in the dissociation of the forward primer and primer binding oligonucleotide. This dissociation, coupled with the primer incorporation into the final PCR product, results in quenching of the intercalating dye by the BHQ®1 quencher and emission of the detectable probe fluorophore Q705.

A quenched control assay was performed under three conditions. Condition 1 (FIG. 3A) was performed as follows: The following components were mixed to create a 20 uL reaction volume: 100 nM of each of the CCND1 primers from Bio-Rad Laboratories Prime PCR products (cat: 10025636), 2 uL of a 1 to 10 dilution of a cDNA preparation from HeLa cells, iTaq Universal SYBR® Green Supermix (Bio-Rad, cat: 1725121). Condition 2 (FIG. 3B) was performed as follows: the reaction contained all of the components in condition 1 plus 300 nM of each of the quencher containing control primers (BioSearch Technologies), 500 nM of the reporter hydrolysis probe containing Quasar 705 at the 5' end and BHQ®3 at the 3' (Biosearch Technologies), and the control template gBlock (Integrated DNA Technologies). Condition 3 (FIG. 3C) was performed as follows: the reaction contained all of the components in condition 1 plus 300 nM of each of the non quencher containing control primers (BioSearch Technologies), 500 nM of the reporter hydrolysis probe containing Quasar 705 at the 5' end and BHQ®3 at the 3' (Biosearch Technologies), and the control template gBlock (Integrated DNA Technologies). For conditions 1 and 2 the control template was present at ~5 ag/rxn. All reactions were carried out in white 96 well PCR plates (Bio Rad, Cat: 9651) on a CFX Real Time qPCR instrument (Bio Rad). The thermal protocol cycled between 95° C. and 58° C. and included a multi-color well read after each 58° C. step. Analysis was carried out using CFX Maestro software version 1.1

(Bio-Rad) and Microsoft Excel.

Figure 3A:
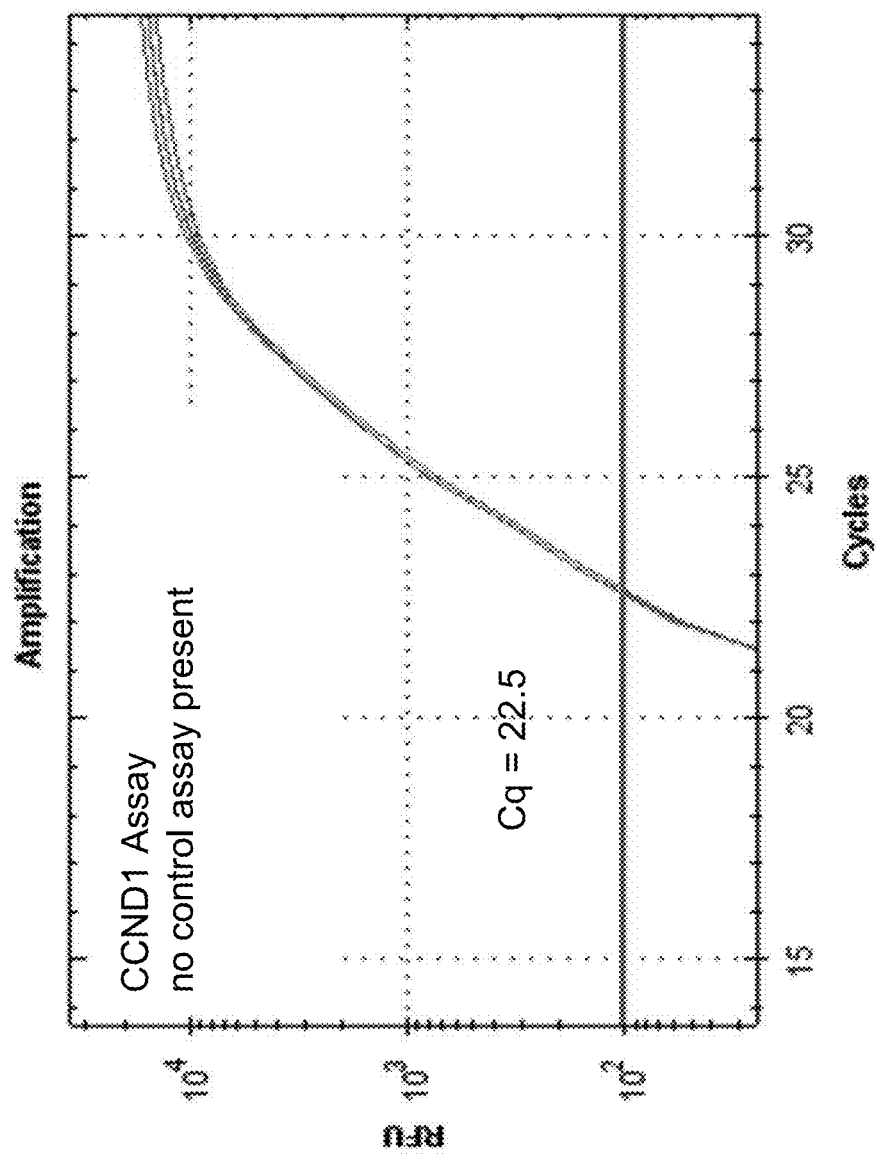
FIG. 3A-3C. (A) CCND1 assay run in the absence of a control assay. (B) CCND1 assay run in the presence of a quenched control assay. (C) CCND1 assay run in the presence of a non-quenched control assay.
Figure 3B:
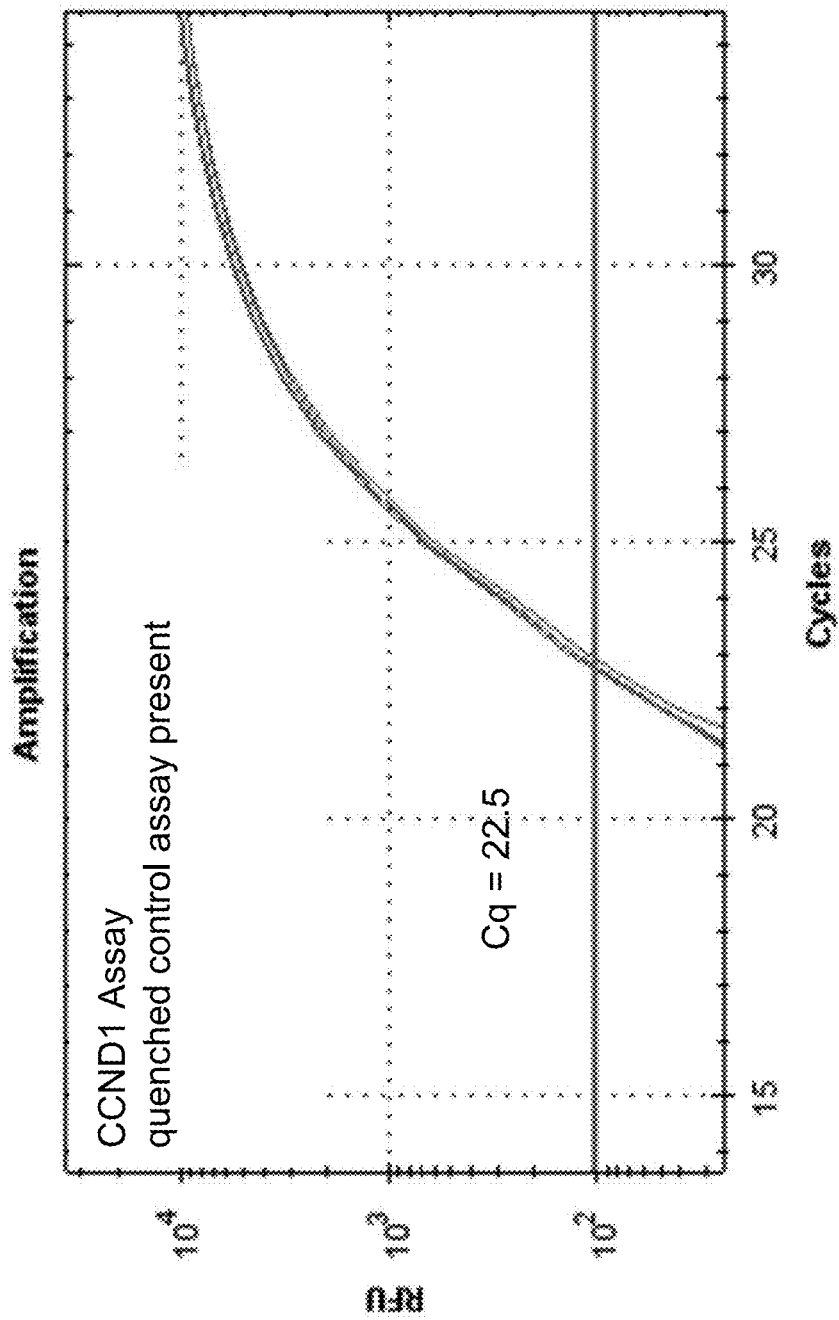
Figure 3C:
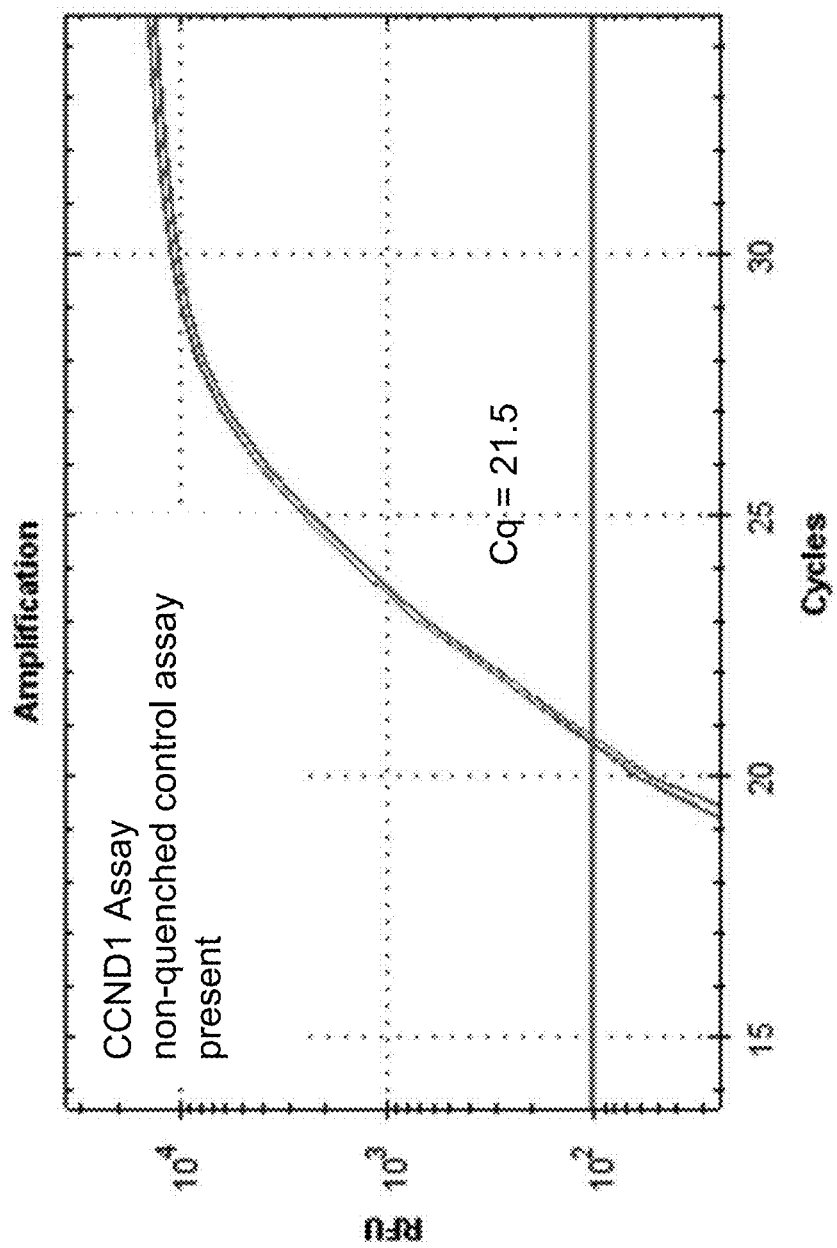

As shown in FIGS. 3A-3B, the use of a quenched control assay allowed for accurate quantitation of a qPCR reaction for a target gene (CCND1). When the CCND1 assay was run in the absence of any control assay (FIG. 3A), the Cq for the qPCR reaction was determined to be 22.5. When the CCND1 assay was run in the presence of a quenched control assay using fluorescence quenching primers as disclosed above, the Cq for the CCND1 assay remained at 22.5 (FIG. 3B). In contrast, and as expected, FIG. 3C shows that the non-quenched control assay (using the same detectable probe and the same control primer sequences, but without quenchers on the primers, as the probe and primers used for FIG. 3B) did impact the Cq measurement for CCND1 (Cq=21.5). Because the Cq measurements are in log 2 scale, a difference of 1 Cq is a significant difference that prevents accurate quantitation of the target.

Figure 4:
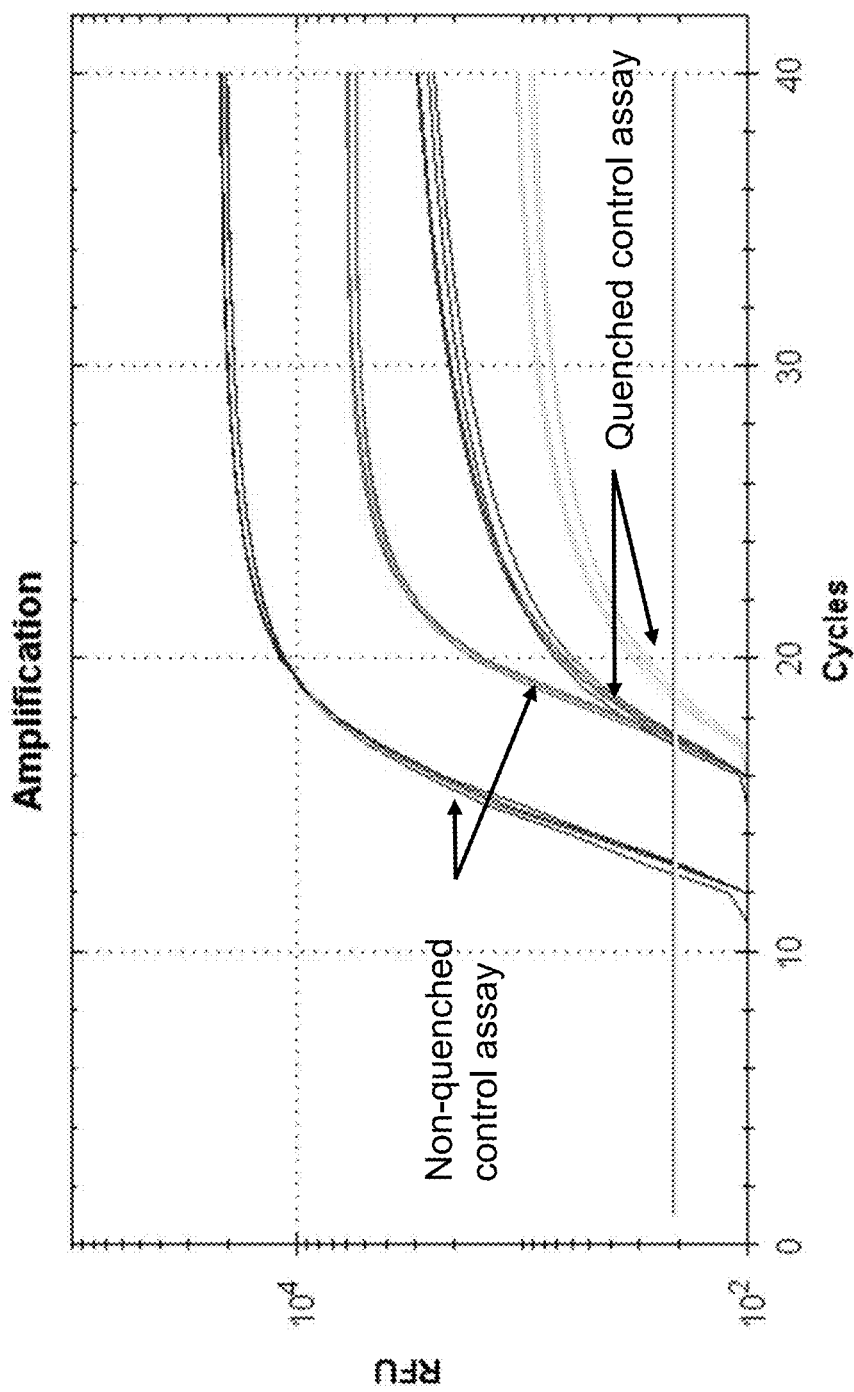
FIG. 4. Example of product-specific quenching in qPCR. The probe fluorescence (in red) produces a single quantitation cycle (Cq), as indicated by the horizontal line, even though the end point amplitude is different. The SYBR® Green fluorescence (in green) shifts by ~6-7 Cq between the non-quenched and quenched control assays. 6 Cq is roughly equivalent to a 40-80× decrease in SYBR Green fluorescence intensity for the quenched assay.

FIG. 4 shows another analysis of quenched versus non-quenched control assays. In this experiment, two conditions were tested. For condition 1, 20 uL reactions were prepared that contained 300 nM of each of the quencher containing control primers (BioSearch Technologies), 500 nM of the reporter hydrolysis probe containing Quasar® 705 at the 5' end and BHQ3 at the 3' (Biosearch Technologies), and the control template gBlock (Integrated DNA Technologies). For condition 2, 20 uL reactions were prepared that contained 300 nM of each of the non quencher containing control primers (BioSearch Technologies), 500 nM of the reporter hydrolysis probe containing Quasar® 705 at the 5' end and BHQ3 at the 3' (Biosearch Technologies), and the control template gBlock (Integrated DNA Technologies). For conditions 1 and 2 the control template was present at ~5 ag/rxn. All reactions were carried out in white 96 well PCR plates (Bio Rad, Cat: 9651) on a CFX Real Time qPCR instrument (Bio Rad). The thermal protocol cycled between 95° C. and 58° C. and included a multi-color well read after each 58° C. step. Analysis was carried out using CFX Maestro software version 1.1 (Bio-Rad) and Microsoft Excel. As shown in FIG. 4, the signal from the detectable probe is shown in red and the signal from the DNA intercalator is shown in green. The probe fluorescence (in red) produces a single Cq even though the end point amplitude is different, indicating that the reaction is operating properly. The DNA intercalator fluorescence (in green) shifts by ~6-7 Cq between the non-quenched and quenched control assays. 6 Cq is roughly equivalent to a 40-80× decrease in SYBR® Green fluorescence intensity for the quenched assay.

Figure 5A:
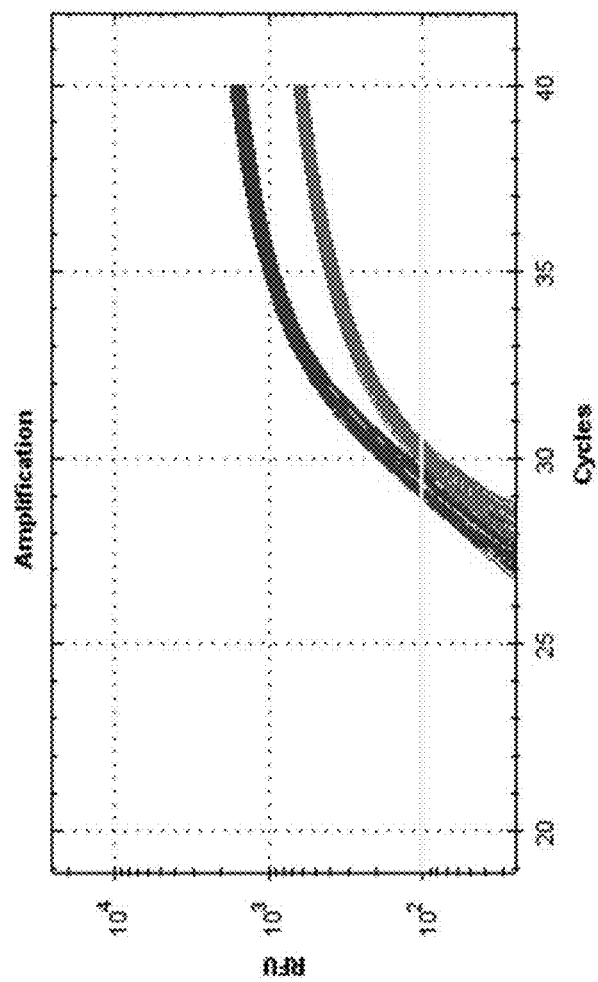
FIG. 5A-5B. Assessment of uniformity in quenched fluorescence qPCR Assay. (A) Graph showing probe signal (in red) and SYBR® Green fluorescence (in green) with no cDNA present. (B) Chart showing probe fluorescence and Cq values that correspond to different standard deviation cut-offs.
Figure 5B:
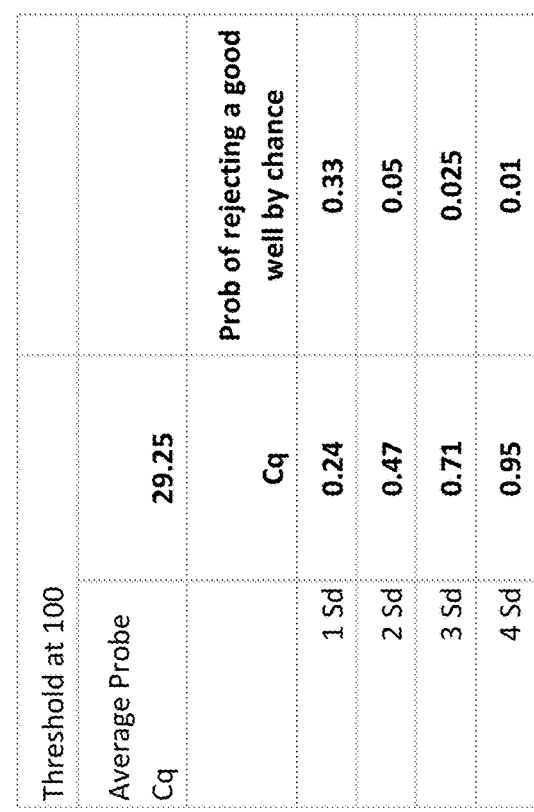

Uniformity for the control assay was assessed as shown in FIG. 5. In this experiment 20 uL reactions were prepared that contained 300 nM of each of the quencher containing control primers (BioSearch Technologies), 500 nM of the reporter hydrolysis probe containing Quasar 705 at the 5' end and BHQ3 at the 3' (Biosearch Technologies), and the control template gBlock (Integrated DNA Technologies). The control template was present at ~5 ag/rxn. A total of 16 wells were prepared as described above. The 16 wells contained 4 cDNA input levels from the HeLa cDNA sample described above for FIG. 3. The cDNA dilution inputs were 1 to 10, 1 to 100, 1 to 1000 and no cDNA. Each condition was equally represented in the plate (4 wells each). All reactions were carried out in white 96 well PCR plates (Bio Rad, Cat: 9651) on a CFX Real Time qPCR instrument (Bio Rad). The thermal protocol cycled between 95° C. and 58° C. and included a multi-color well read after each 58° C. step. Analysis was carried out using CFX Maestro software version 1.1 (Bio-Rad) and Microsoft Excel. As shown in FIG. 5A, the control assay exhibited good uniformity. FIG. 5B shows Cq values corresponding to various standard deviation cut-offs and the probability that a "good" well (e.g., a non-inhibited well) would be rejected by chance at the different standard deviation cut-offs.

Example 2: Heparin Titration Study of Inhibition

Reaction inhibition can prevent the accurate quantitation of a qPCR assay. One known inhibitor of PCR reactions is heparin. A heparin titration study was conducted to determine whether the quenched control assays disclosed herein can be used to detect heparin inhibition.

Figure 6A:
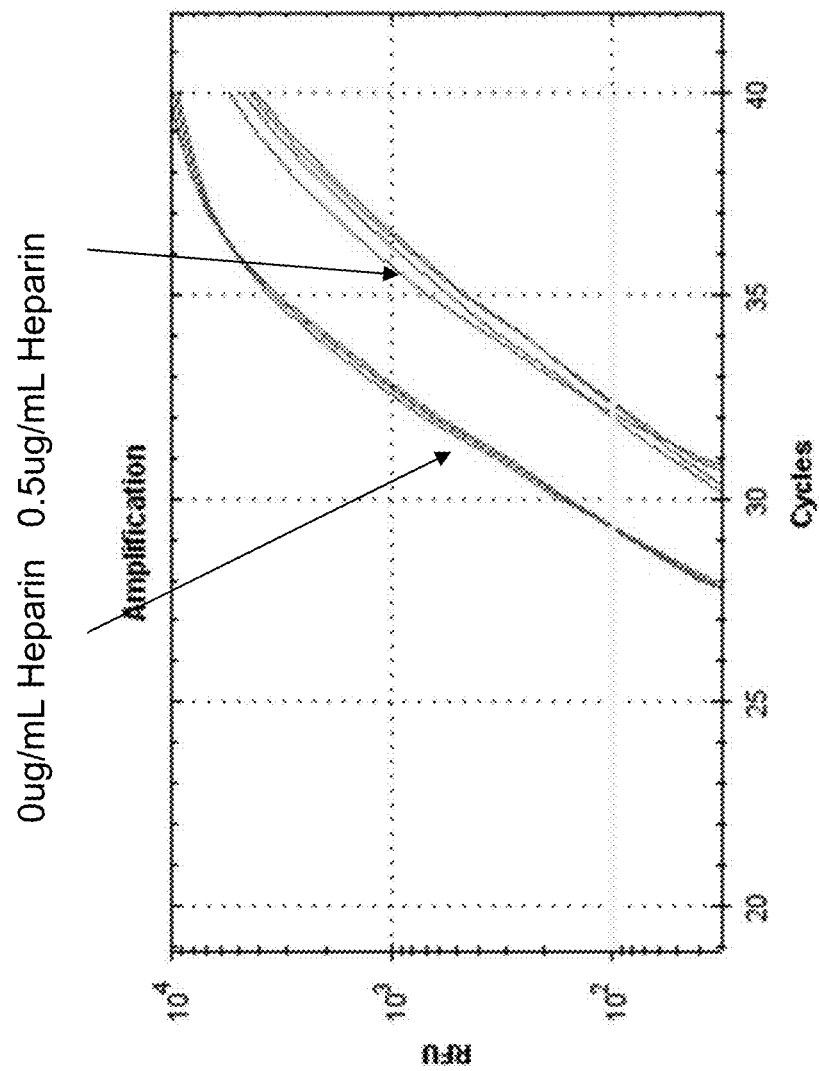
FIG. 6A-6B. Effect of heparin on SYBR® Green fluorescence in a p53 gene of interest assay. (A) p53 assay in the absence of a control assay. (B) p53 assay in the presence of a quenched control assay.
Figure 6B:
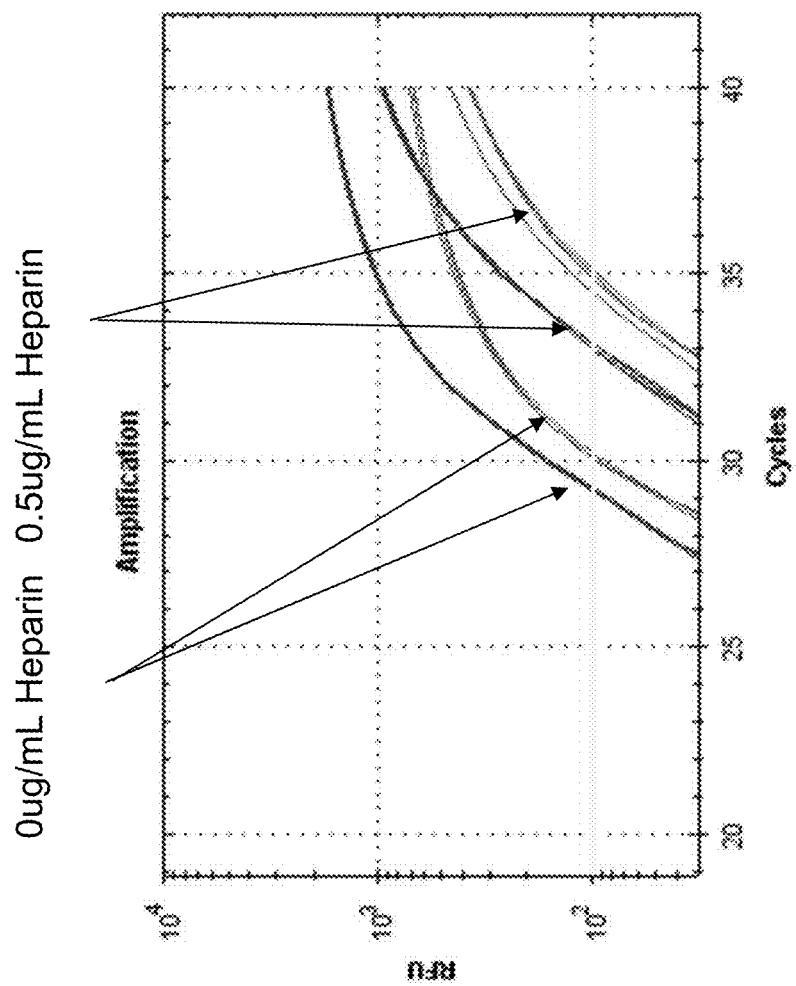

FIG. 6 shows the effect of an inhibitor (heparin) on fluorescence signal and shows that quenched control assays can be used to detect reaction inhibition. In this experiment the effects of a PCR inhibitor, heparin, were tested under two reaction conditions. For condition 1 (FIG. 6A), the following components were mixed to create a 20 uL reaction volume: 100 nM of each of the CCND1 primers from Bio-Rad Laboratories Prime PCR products (cat: 10025636), 2 uL of a 1 to 10 dilution of a cDNA preparation from HeLa cells, iTaq Universal SYBR® Green Supermix (Bio-Rad, cat: 1725121). For condition 2 (FIG. 6B), the reaction mixture contained all of the components in condition 1 plus 300 nM of each of the quencher containing control primers (BioSearch Technologies), 500 nM of the reporter hydrolysis probe containing Quasar 705 at the 5' end and BHQ3 at the 3' (Biosearch Technologies), and the control template gBlock (Integrated DNA Technologies). For condition 2 the control template was present at ~5 ag/rxn. For each condition the samples were challenged with either 0.5 ug/mL Heparin (Sigma Aldrich) or with a mock treatment of equal volume. All reactions were carried out in white 96 well PCR plates (Bio Rad, Cat: 9651) on a CFX Real Time qPCR instrument (Bio Rad). The thermal protocol cycled between 95° C. and 58° C. and included a multi-color well read after each 58° C. step. Analysis was carried out using CFX Maestro software version 1.1 (Bio-Rad) and Microsoft Excel.

FIG. 6A-6B shows that for both the p53 gene of interest assay and the quenched control assay, there was a 3-5 Cq shift in the presence of heparin. In FIG. 6B, the detectable probe (Quasar) signal and the SYBR® Green signal both demonstrated an approximately equal Cq shift, indicating that the reaction was generally inhibited. Thus, the quenched control assay can effectively detect reaction inhibition through the detectable probe assay, allowing the well to be rejected.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

quenchers quench all or substantially all of the fluorescence from an amplification product of the control nucleic acid;
a detectable probe that specifically associates with the control nucleic acid; and
the control nucleic acid, wherein the control nucleic acid comprises a forward primer binding site to which the forward quenching primer binds, a probe binding site to which the detectable probe binds, and a reverse primer binding site to which the reverse quenching primer binds.

2. The composition of claim 1, wherein:
for the forward quenching primer, the first quencher is at the 5' end or is within 5 bases from the 5' end and the second quencher is within 5-10 bases from the 3' end; and/or
for the reverse quenching primer, the first quencher is at the 5' end or is within 5 bases from the 5' end and the second quencher is within 5-10 bases from the 3' end.

3. The composition of claim 1, wherein the detectable probe directly binds to the control nucleic acid.

4. The composition of claim 1, wherein:
the detectable probe is attached to the forward quenching primer and/or the reverse quenching primer; or
the detectable probe is attached to an oligonucleotide that hybridizes to a portion of the forward quenching primer or the reverse quenching primer.

5. The composition of claim 1, further comprising a fluorescent DNA intercalator.

6. The composition of claim 5, wherein the fluorescent DNA intercalator is N',N'-dimethyl-N-[4-[(E)-(3-methyl-1,3-benzothiazol-2-ylidene)methyl]-1-phenylquinolin-1-ium-2-yl]-N-propylpropane-1,3-diamine, 2-[Bis[3-(dimethylamino)propyl]amino]-4-[(3-methyl-2(3H)-benzothiazolylidene)methyl]-1-phenylquinolinium, ethidium bromide, unsymmetrical cyanine dye 2-[N-(3-dimethylaminopropyl)-N-propylamino]-4-[2,3-dihydro-3-

What is claimed is:

1. A composition for normalizing a quantitative polymerase chain reaction (PCR) amplification, comprising:
a set of fluorescence quenching primers that specifically bind to a control nucleic acid, the set comprising a forward quenching primer and a reverse quenching primer, wherein each of the forward quenching primer and the reverse quenching primer comprises two or more quenchers and wherein the two or more quenchers are positioned within the primer such that the methyl-(benzo-1,3-thiazol-2-yl)-methylidene]-1-phenyl-quinolinium, 1,1'-(4,4,7,7-Tetramethyl-4,7-diazaundecamethylene)-bis-4-(3-methyl-2,3-dihydro-(benzo-1,3-oxazole)-2-methylidene)-quinolinium tetraiodide, 4-[(3-methyl-1,3-benzoxazol-2(3H)-ylidene)methyl]-1-[3-(trimethylammonio)propyl]quinolinium diiodide, 1,1' (4,4,7,7-tetramethyl-4,7-diazaundecamethylene) bis-4-(3-methyl-2,3-dihydro(benzo-1,3-thiazole)-2-methylidene)quinolinium, 4-[6-(Benzoxazol-2-yl)-dihydro-3-methyl-2(3H)-benzothiazolylidenemethyl]-1- methylquinolinium iodide, or 4-[(3-methyl-6-(benzothiazol-2-yl)-2,3-dihydro-(benzo-1,3-thiazole)-2-methylidene)]1-methyl-pyridinium iodide.

7. The composition of claim 5, wherein the detectable probe comprises a fluorescent dye having an emission spectrum that is distinguishable from the emission spectrum of the fluorescent DNA intercalator.

8. The composition of claim 1, wherein the detectable probe comprises:
  a fluorescent dye selected from the group consisting of 1,1'-bis(3-hydroxypropyl)-3,3,3',3'-tetramethylindocarbocyanine), 1,1'-bis(3-hydroxypropyl)-3,3,3 ',3'-tetramethylindodicarbocyanine, carboxyfluorescein, 4,7,2',4',5',7'-hexachloro-6-carboxy-fluorescein, 6-carboxy-4'-, 5'-dichloro-2'-, 7'-dimethoxy-fluorescein, indocarbocyanines-Q, rhodamine, 5 and 6-carboxy-X-rhodamine, N,N,N',N'-tetramethyl-6-carboxyrhodamine, 4,7,2',7'-tetrachloro-6-carboxy-fluorescein, sulforhodamine 101 acid chloride, and 2'-chloro-7'phenyl-1,4-dichloro-6-carboxy-fluorescein; and/or
  a hydrolysis probe.

9. A solid support comprising one or more partitions, wherein each of the one or more partitions comprises the composition of claim 1.

10. A kit comprising the composition of claim 1 or the solid support of claim 9.

11. A method for normalizing a qPCR amplification to a control, the method comprising:
  combining a target nucleic acid and a control nucleic acid with (i) a fluorescent DNA intercalator, (ii) a set of target nucleic acid-specific primers comprising a target nucleic acid-specific forward primer and a target nucleic acid-specific reverse primer, (iii) a detectable probe that specifically associates with the control nucleic acid, and (iv) a set of fluorescence quenching primers that specifically bind to a control nucleic acid comprising a forward quenching primer and a reverse quenching primer, wherein each of the forward quenching primer and the reverse quenching primer comprises two or more quenchers and wherein the two or more quenchers are positioned within the primer such that the quenchers quench all or substantially all of the fluorescence from an amplification product of the control nucleic acid, thereby forming a reaction mixture;
  incubating the reaction mixture under conditions suitable to generate a target nucleic acid amplicon and a control nucleic acid amplicon, wherein the fluorescent DNA intercalator binds to both the target nucleic acid amplicon and the control nucleic acid amplicon and wherein the control nucleic acid amplicon that is generated comprises a plurality of quenchers incorporated into the amplicon;
  exciting the fluorescent DNA intercalator, wherein the quenchers that are incorporated into the control nucleic acid amplicon quench at least a portion of the fluorescence emitted by the fluorescent DNA intercalator bound to the control nucleic acid amplicon; and
  detecting the target nucleic acid amplicon and the control nucleic acid amplicon, wherein the target nucleic acid amplicon is detected by detecting the fluorescent signal emitted by the fluorescent DNA intercalator and wherein the control nucleic acid amplicon is detected by detecting the detectable probe.

12. The method of claim 11, wherein each of the forward quenching primer and the reverse quenching primer comprises a first quencher at or near the 5' end of the primer and a second quencher near the 3' end of the primer.

13. The method of claim 11, wherein the detectable probe directly binds to the control nucleic acid.

14. The method of claim 11, wherein:
  (i) the detectable probe is attached to the forward quenching primer and/or the reverse quenching primer; or
  (ii) the detectable probe is attached to an oligonucleotide that hybridizes to a portion of the forward quenching primer or the reverse quenching primer.

15. The method of claim 11, wherein the detecting step comprises quantitating the amount of fluorescent signal emitted by the fluorescent DNA intercalator and the amount of signal from the detectable probe.

16. A method for multiplexing qPCR amplification of two target nucleic acids in the same well, the method comprising:
  combining a sample comprising a first target nucleic acid and a second target nucleic acid with (i) a fluorescent DNA intercalator, (ii) a first target nucleic acid-specific primer set comprising a first target nucleic acid-specific forward primer and a first target nucleic acid-specific reverse primer, (iii) a detectable probe that specifically associates with the second target nucleic acid, and (iv) a second target nucleic acid-specific primer set comprising a forward quenching primer and a reverse quenching primer that specifically bind to the second target nucleic acid, wherein each of the forward quenching primer and the reverse quenching primer comprises two or more quenchers and wherein the two or more quenchers are positioned within the primer such that the quenchers quench all or substantially all of the fluorescence from an amplification product of the second target nucleic acid, thereby forming a reaction mixture;
  incubating the reaction mixture under conditions suitable to generate a first target nucleic acid amplicon and a second target nucleic acid amplicon, wherein the fluorescent DNA intercalator binds to both the first target nucleic acid amplicon and the second target nucleic acid amplicon and wherein the second target nucleic acid amplicon that is generated comprises a plurality of quenchers incorporated into the amplicon;
  exciting the fluorescent DNA intercalator, wherein the quenchers in the second target nucleic acid amplicon quench at least a portion of the fluorescence emitted by the fluorescent DNA intercalator bound to the second target nucleic acid amplicon; and
  detecting the first target nucleic acid amplicon and the second target nucleic acid amplicon, wherein the first target nucleic acid amplicon is detected by detecting the fluorescent signal emitted by the fluorescent DNA intercalator and wherein the second target nucleic acid amplicon is detected by detecting the detectable probe.

17. The method of claim 16, wherein the detectable probe directly binds to the second target nucleic acid.

18. The method of claim 16, wherein:
  (i) the detectable probe is attached to the forward quenching primer and/or the reverse quenching primer; or
  (ii) the detectable probe is attached to an oligonucleotide that hybridizes to a portion of the forward quenching primer or the reverse quenching primer.

19. The method of claim 16, wherein the detectable probe comprises a fluorescent dye having an emission spectrum that is distinguishable from the emission spectrum of the fluorescent DNA intercalator.

20. The method of claim 16, wherein the detecting step comprises quantitating the amount of fluorescent signal emitted by the fluorescent DNA intercalator and the amount of signal from the detectable probe.

* * * * *

SEQUENCE LISTING

<160> NUMBER OF SEQ ID NOS: 1

<210> SEQ ID NO 1
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
tggacattgt cgatccgcgt gaaagttagg tggaatcgca tcatagcccc gttctaggct     60
ctccgacggc actatctaag gctctgtcaa caaaacgtat ccagtggtat gccgtgtatt    120
gtaatg                                                              126
```